US012622820B2

(12) United States Patent
Ebert et al.

(10) Patent No.: US 12,622,820 B2
(45) Date of Patent: May 12, 2026

(54) FEMININE HYGIENE PAD WITH DIFFERING FUNCTIONAL ARRANGEMENTS OF TOPSHEET APERTURES

(71) Applicant: The Procter & Gamble Company, Cincinnati, OH (US)

(72) Inventors: Debora Christine Ebert, Blanchester, OH (US); Misael Omar Aviles, Hamilton, OH (US); Rong Deng, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 591 days.

(21) Appl. No.: 17/976,964

(22) Filed: Oct. 31, 2022

(65) Prior Publication Data
US 2024/0139041 A1      May 2, 2024

(51) Int. Cl.
*A61F 13/15*      (2006.01)
*A61F 13/512*      (2006.01)
*A61F 13/537*      (2006.01)
*A61F 13/51*      (2006.01)
*A61F 13/513*      (2006.01)

(52) U.S. Cl.
CPC .... *A61F 13/5126* (2013.01); *A61F 13/15707* (2013.01); *A61F 13/15764* (2013.01); *A61F 13/5123* (2013.01); *A61F 13/53747* (2013.01); *A61F 2013/51019* (2013.01);
(Continued)

(58) Field of Classification Search
CPC ............ A61F 13/5126; A61F 13/15707; A61F 13/15764; A61F 13/5123; A61F

13/53747; A61F 2013/51019; A61F 2013/51023; A61F 2013/5127; A61F 2013/51366

See application file for complete search history.

(56) References Cited

U.S. PATENT DOCUMENTS

2003/0125687 A1*    7/2003    Gubernick .......... A61F 13/2051
                                                          604/383
2009/0259208 A1*  10/2009    Hellstrom .............. D04H 1/492
                                                          604/383

(Continued)

OTHER PUBLICATIONS

PCT Search Report and Written Opinion for PCT/US2023/078157 dated Feb. 12, 2024, 9 pages.

*Primary Examiner* — Jacqueline F Stephens
(74) *Attorney, Agent, or Firm* — Sarah M. DeCristofaro

(57)      ABSTRACT

A feminine hygiene pad is disclosed. The disclosed pad has a longitudinal axis and a lateral axis, and has a topsheet including a nonwoven web, a backsheet, and an absorbent structure between the topsheet and the backsheet. The nonwoven web includes at least a first arrangement of first apertures having a first average size, and a second arrangement of second apertures having a second average size. The first average size is greater than the second average size. The first arrangement occupies a rectangular central region centered about the longitudinal axis and straddling the lateral axis. The first average size is 0.4 mm² to 0.6 mm²; and the central region has an Average Percent Open Area of 1 to 12 percent. The second arrangement occupies one or more regions laterally and/or longitudinally outboard of the central region, and the second average size is 0.05 mm² to 0.2 mm².

23 Claims, 16 Drawing Sheets

(52) U.S. Cl.

CPC .............. *A61F 2013/51023* (2013.01); *A61F 2013/5127* (2013.01); *A61F 2013/51366* (2013.01)

(56) References Cited

U.S. PATENT DOCUMENTS

| | | | |
|---|---|---|---|
| 2011/0106036 A1* | 5/2011 | Stahl .................... | A61F 13/515 604/383 |
| 2013/0144241 A1* | 6/2013 | Persson ............ | A61F 13/53713 604/378 |
| 2014/0324009 A1 | 10/2014 | Lee | |
| 2016/0067118 A1* | 3/2016 | Hammons ................ | B32B 3/30 428/137 |
| 2018/0229216 A1 | 8/2018 | Smith et al. | |
| 2019/0314218 A1* | 10/2019 | Arora ............... | A61F 13/15764 |

* cited by examiner

FEMININE HYGIENE PAD WITH DIFFERING FUNCTIONAL ARRANGEMENTS OF TOPSHEET APERTURES

BACKGROUND

Feminine hygiene pads, also sometimes known as sanitary napkins, have been marketed, and in use for many years, by women for purposes of intercepting and absorbing menstrual discharge, and preventing soiling of underwear, outer clothing, bedclothes, etc. Manufacturers of feminine hygiene pads continuously strive to improve the products to improve performance and consumer/user satisfaction.

A focus of attention for development has been pad topsheet material. Generally, users prefer material that feels soft, pliable and comfortable against the skin; is breathable and does not have a plastic film-like feel; functions to rapidly receive and pass discharged menstrual fluid downwardly therethrough to absorbent components beneath, and alone or in combination with underlying components, maintains a relatively dry feel after a discharge, through a combination of rapid transfer of discharged fluid down to underlying absorbent components, avoidance of absorbing fluid itself, and avoidance or resistance to "re-wetting" by fluid residing in the absorbent components. For some users, it may be important that the topsheet have some opacity and resulting ability to reduce visibility of staining of the absorbent components by absorbed fluid, to the greatest extent feasible.

Because these functional objectives for topsheet material are often somewhat in tension with each other with respect to material performance characteristics, producing a topsheet material that fully meets all of these objectives remains a challenge, and opportunity for improvement continues to exist.

DESCRIPTION OF EXAMPLES

Definitions

Figure 1:
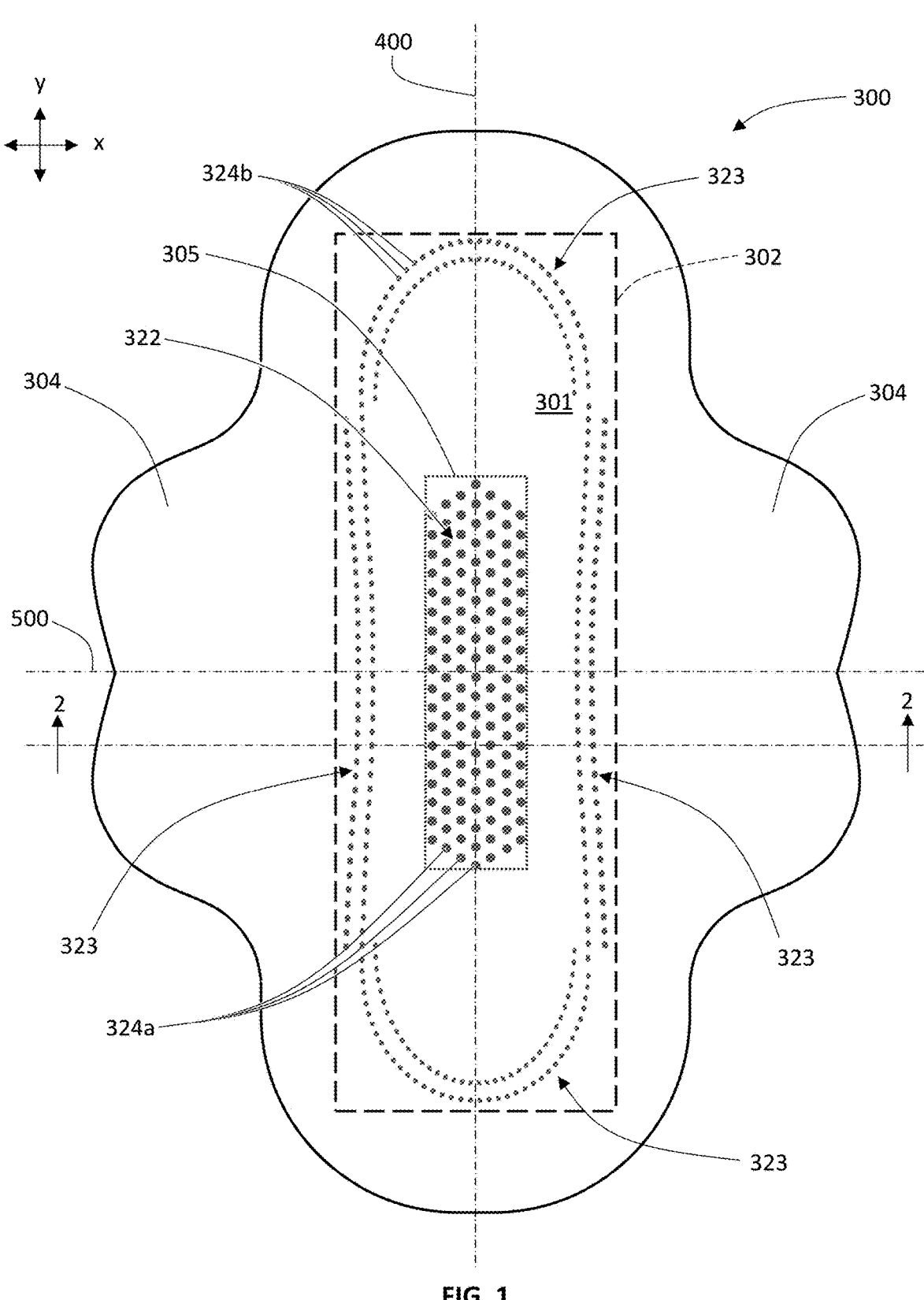
FIG. 1 is a schematic plan view depiction of an example of an absorbent article in the form of a feminine hygiene pad.

As used herein, the following terms shall have the meaning specified thereafter:

The term "integrated" as used herein is used to describe fibers of a nonwoven material which have been intertwined, entangled, and/or pushed/pulled in a positive and/or negative Z-direction (direction of the thickness of the nonwoven material). Some exemplary processes for integrating fibers of a nonwoven web include spunlacing and needlepunching. Spunlacing (also known as "hydroentangling" or ("hydroenhancing") uses a plurality of high pressure water jets directed at a precursor batt or accumulation of fibers being conveyed along a machine direction, to entangle the fibers. Needlepunching (also known as "needling") involves the use of specially-featured needles to mechanically push and/or pull fibers, of a precursor batt or accumulation of fibers, in a z-direction, to entangle them with other fibers in the batt or accumulation.

The term "carded" as used herein is used to describe structural features of particular types of nonwoven web materials contemplated herein for use in some examples as apertured topsheet material. A carded nonwoven web is formed of fibers which are cut to a specific finite length, otherwise known as "staple length fibers." Staple length fibers may be of any selected length. For example, staple length fibers may be cut to a length of up to 120 mm, to a length as short as 10 mm. However, if fibers of a particular group are staple length fibers, then the length of each of the fibers in the carded nonwoven is approximately the same, i.e. the staple length. Where fibers of more than one composition are included in a nonwoven web, for example, a web including polypropylene fibers and viscose fibers, the length of each fiber of the same composition may be substantially the same, while the respective staple fiber lengths of the respective fiber compositions may differ.

In contrast to staple fibers, filaments such as those produced by spinning, e.g., in a spunbond or meltblown nonwoven web manufacturing processes, are not ordinarily staple length fibers. Instead, these filaments are sometimes characterized as "continuous" fibers, meaning that they are of a relatively long and indeterminate length, not cut to a specific length following spinning, as their staple fiber counterparts are.

"Lateral"—with respect to a feminine hygiene pad, or a component thereof, refers to a direction parallel to a horizontal line tangent to the front surfaces of the upper portions of wearer's legs proximate the torso, when the pad is being worn normally and the wearer has assumed an even, square, normal standing position. A "width" dimension of any component or feature of a feminine hygiene pad is measured along the lateral direction. When the pad or component thereof is laid out flat on a horizontal surface, the "lateral" direction corresponds with the lateral direction relative the structure when it is worn, as defined above. With respect to a feminine hygiene pad that is opened and laid out flat on a horizontal planar surface, "lateral" refers to a direction perpendicular to the longitudinal direction and parallel to the horizontal planar surface. With respect to a feminine hygiene pad, the "x-direction" is also the lateral direction.

The "lateral axis" of a feminine hygiene pad or component thereof is a lateral line lying in an x-y plane and equally dividing the length of the pad or the component when it is laid out flat on a horizontal surface. A lateral axis 500 (see FIG. 1) is perpendicular to a longitudinal axis 400.

"Longitudinal"—with respect to a feminine hygiene pad, or a component thereof, refers to a direction perpendicular to the lateral direction. A "length" dimension of any component or feature of the pad is measured along the longitudinal direction from its forward extent to its rearward extent. When a feminine hygiene pad or component thereof is laid out flat on a horizontal surface, the "longitudinal" direction is perpendicular to the lateral direction relative the pad when it is worn, as defined above. With respect to a pad, the "y-direction" is also the longitudinal direction.

The "longitudinal axis" of a feminine hygiene pad is a longitudinal line lying in an x-y plane and equally dividing the width of the pad or component, when the pad is laid out flat on a horizontal surface. A longitudinal axis 400 (see FIG. 1) is perpendicular to a lateral axis 500.

Figure 14:
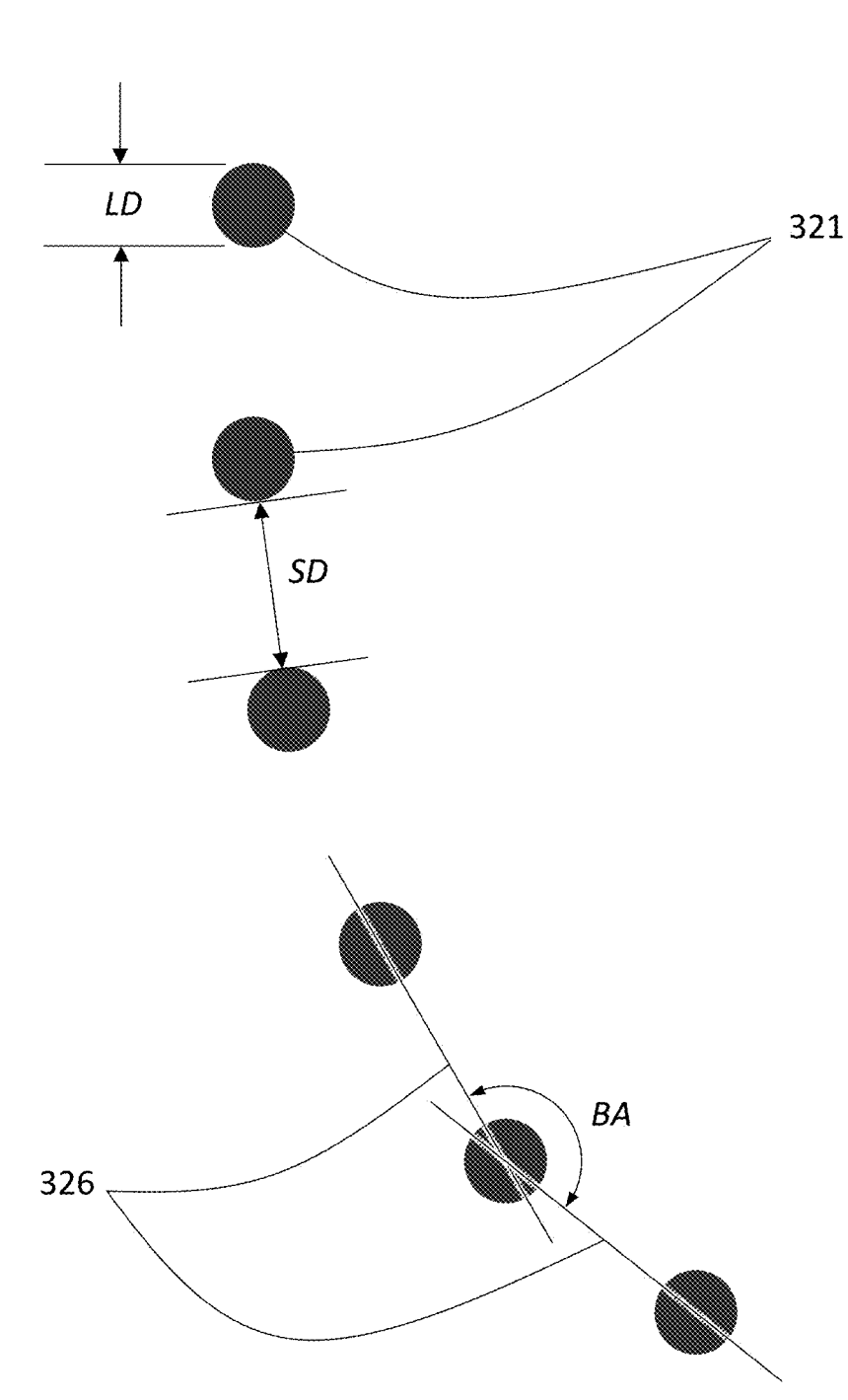
FIG. 14 is a schematic expanded plan view (along a z-direction) of an example of a path of apertures.

A "path" of apertures is a group of five or more apertures 321 having the following features, illustrated by way of example in FIG. 14:

Each aperture in the group of five or more is located a distance SD that is no greater than 3 times the largest x-y dimension LD of apertures in the group, from its farthest immediate neighbor, where distance SD is measured between closest portions of perimeters of the neighboring apertures.

There is no break angle BA among the group that is less than 120 degrees, where the break angle BA is the larger angle at the intersection of path lines 326 through the geometric centers of immediately neighboring apertures, along an x-y plane.

The relative terms "outboard" and "inboard" relate to locations on a pad along x-y directions, relative to the longitudinal axis 400 and lateral axis 500 of the pad, wherein the intersection of the longitudinal and lateral axes is the laterally and longitudinally inboard-most location on the pad, and all locations of the pad that are spaced away from this intersection are outboard of it. The outboard-most locations of a pad lie along its perimeter edge. A first location is inboard of a second location and the second location is outboard of the first location, when the first location lies closer to the intersection than the second location, and both locations are on the same sides of the longitudinal and lateral axes. A first location is laterally inboard of a second location and the second location is laterally outboard of the first location, when the first location lies closer to the longitudinal axis than the second location, and both locations are on the same side of the longitudinal axis. A first location is longitudinally inboard of a second location and the second location is longitudinally outboard of the first location, when the first location lies closer to the lateral axis than the second location, and both locations are on the same side of the lateral axis.

The "size" of an aperture is the greatest x-y plane dimension of its perimeter. By way of non-limiting example, the size of an aperture with a circular perimeter is the diameter of the perimeter. In another non-limiting example, the size of an aperture with an oval-shaped perimeter is the length of the greater axis of the oval shape.

"x-y plane," with reference to a feminine hygiene pad, or component thereof, when laid out flat on a horizontal surface, means any horizontal plane occupied by the horizontal surface or any layer of the pad or component.

"z-direction," with reference to a feminine hygiene pad or component thereof, when laid out flat on a horizontal surface, is a direction perpendicular/orthogonal to the x-y plane.

The terms "top," "bottom," "upper," "lower," "over," "under," "beneath," "superadjacent," "subjacent," and similar terms characterizing relative vertical positioning, when used herein to refer to layers, components or other features of a feminine hygiene pad, relate to positioning along the z-direction and are to be interpreted with respect to the pad as it would appear when laid out flat on a horizontal surface, with its wearer-facing surface oriented upward and outward-facing surface oriented downward.

With respect to a feminine hygiene pad, or a component or structure thereof, "wearer-facing" is a relative locational term referring to a feature of the component or structure that when in use lies closer to the wearer than another feature of the component or structure. For example, a topsheet has a wearer-facing surface that lies closer to the wearer than the opposite, outward-facing surface of the topsheet.

With respect to a feminine hygiene pad, or a component or structure thereof, "outward-facing" is a relative locational term referring to a feature of the component or structure that when in use lies farther from the wearer than another feature of the component or structure. For example, a topsheet has an outward-facing surface that lies farther from the wearer than the opposite, wearer-facing surface of the topsheet.

"Machine direction" or "MD" as used herein with respect to a feminine hygiene pad or component thereof, refers to a direction parallel to the flow of the pad or component through processing/manufacturing equipment. With respect to manufacture of a web material, the "y-direction" is a direction parallel with the machine direction.

"Cross direction" or "CD" as used herein with respect to a feminine hygiene pad or component thereof, refers to a direction perpendicular/orthogonal to the machine direction and to the z-direction. With respect to manufacture of a web material, the "x-direction" is a direction parallel with the cross direction.

"Predominant," and forms thereof, when used to characterize a quantity of weight, volume, surface area, etc., of a feminine hygiene pad or component thereof, constituted by a composition, material, feature, etc., means that a majority of such weight, volume, surface area, etc., of the pad or component thereof is constituted by the composition, material, feature, etc.

General—Feminine Hygiene Pad

Figure 2A:
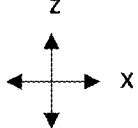
FIG. 2A is a schematic lateral cross section of one non-limiting example of the feminine hygiene pad of FIG. 1, taken through line 2-2 in FIG. 1.
Figure 2A:
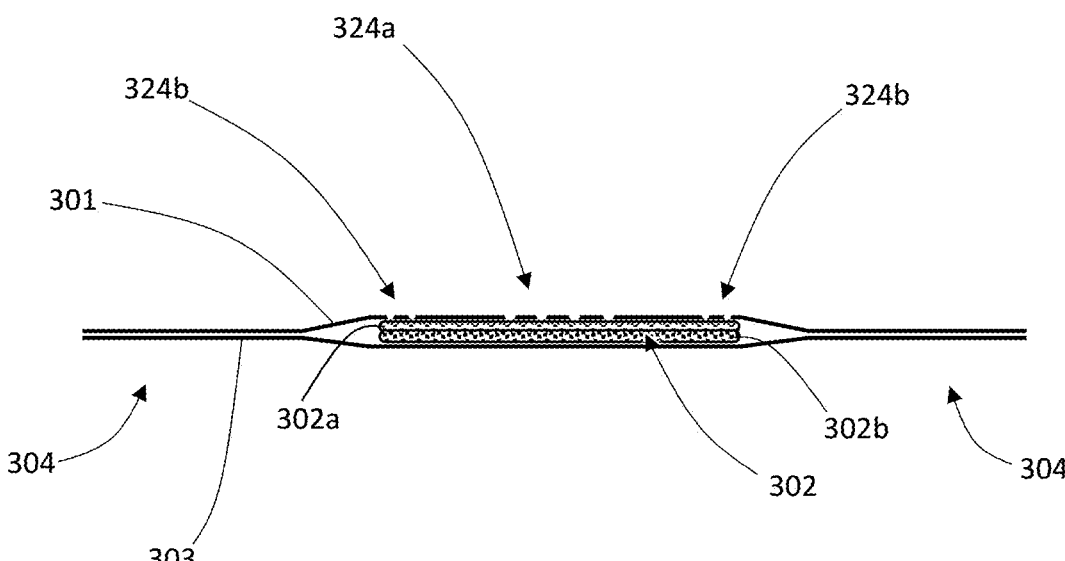

Referring to FIGS. 1 and 2A, a feminine hygiene pad 300, as contemplated herein, will have a longitudinal axis 400 and a lateral axis 500, and include a wearer-facing surface and an opposing outward-facing surface. A liquid permeable topsheet 301 may form at least a portion of the wearer-facing surface and a liquid impermeable backsheet 303 may form at least a portion of the outward-facing surface. An absorbent structure 302 is disposed between the topsheet and the backsheet. The absorbent structure 302 may include a fluid management layer 302*a* and a storage layer 302*b*. (A fluid management layer 302 as described herein is sometimes known in the art as an "acquisition/distribution layer" "distribution layer" or "secondary topsheet", whose purpose is to dissipate energy from a fluid gush to the extent needed, provide a volume of space for discharged fluid to temporarily occupy during the time required for an underlying absorbent structure (e.g., a storage layer) to imbibe and absorb the fluid, and to distribute the fluid across the absorbent structure to maximize effective and efficient use thereof.) Non-limiting examples of absorbent articles sharing these features include feminine hygiene pads, disposable incontinence pads, disposable incontinence underwear, disposable baby diapers and disposable baby/child training pants. Non-limiting examples of suitable absorbent structures/storage layers are described in co-pending U.S. Prov. App. Ser. No. 63/256,164, which is incorporated by reference herein. Non-limiting examples of suitable absorbent structures/storage layers are described in co-pending U.S. Prov. App. Ser. No. 63/316,097, which is incorporated by reference herein.

The topsheet 301 and the backsheet 303 may be joined together to form and define an outer periphery of the pad. The absorbent structure 302 and components or layers thereof (e.g., fluid management layer 302*a* and storage layer 302*b*) will be sized such that their outer perimeters are disposed laterally and longitudinally inboard of the outer periphery. Components or layers of the absorbent structure 302 may be dimensioned and shaped substantially similarly or identically to each other in the x-y directions, or they may have respective differing x-y dimensions and/or shapes. Individual layers may be manufactured to have a rectangular shape as suggested in FIG. 1, or one or both may be manufactured to have any other suitable shape, such as an oval shape, stadium shape, rounded rectangle shape, hourglass shape, peanut shape, etc. Shapes having concave profiles along the longitudinal edges (for example, an hourglass shape) may in some examples provide for enhanced comfort and/or conformity with the wearer's body between the legs.

The topsheet 301 may be joined to the backsheet 303 by any suitable attachment mechanism. The topsheet 301 and the backsheet 303 may be joined directly to each other in the pad periphery, and may be indirectly joined together by directly joining them to the absorbent structure 302, the fluid management layer 302*a* and/or storage layer 302*b*, and/or additional layers disposed between the topsheet 301 and the backsheet 303. This indirect or direct joining may be accomplished by any suitable attachment mechanism known in the art. Non-limiting examples of attachment mechanisms may include e.g. fusion bonds, ultrasonic bonds, pressure bonds, adhesive bonds, or any suitable combination thereof.

Pad 300 may include a pair of oppositely disposed lateral extensions (sometimes called "wings") 304 which do not include absorbent components. Wings 304 may be formed of or include lateral extensions of one or both of the topsheet 301 and the backsheet 303 materials. Wings 304 may also include deposits of an adhesive (not shown) on the outward-facing surfaces thereof. With this configuration, a user may appropriately locate and place pad 300 within the crotch region of her underpants, and wrap and fold wings 304 down, over and around the respective edges of the leg openings, and then adhere the wings 304 to the outside/underside of the underpants crotch region. So positioned, the wings 304 can help hold the pad in suitable position during wear/use, and help protect the underpants from soiling about the leg edges.

Topsheet

General

Generally it is desirable that the topsheet 301 be compliant, soft feeling, and non-irritating to the wearer's skin. A suitable topsheet material will include a liquid pervious material that is disposed to the wearer-facing side of the pad, in a position in which it will contact the body of the wearer. Preferably, the topsheet will be configured to permit discharged fluid to penetrate through it as rapidly as can be effectuated, and desirably, not readily allow fluid to move back up through the topsheet and contact the wearer's skin. The topsheet may also be adapted to bear and/or provide for transfer or migration of a selected lotion composition provided with the pad, to the wearer's skin. The topsheet may include or be formed of a nonwoven material.

Nonwoven webs to be used as components of topsheets may be produced by any known procedure for making nonwoven webs, nonlimiting examples of which include spunbond processes, carding, wet-laying, air-laying, meltblowing processes, needle-punching, mechanical entangling, thermo-mechanical entangling, and hydroentangling.

Nonwoven materials suitable for use as a topsheet component material may include one stratum of accumulated fibers, or may be a laminate or combination of multiple strata of accumulated fibers, which may include similar or different compositions (e.g., spunbond-meltblown laminate). In one specific example, the topsheet may be formed of a carded, air-through bonded nonwoven web material.

Topsheets contemplated herein do not include any predominant fraction of topsheet x-y surface area occupied by film. Some currently known topsheets for feminine hygiene pads include an apertured film, such as a hydroformed film or vacuum-formed film, alone or in combination with an adjacently-disposed nonwoven web material. The film may help to prevent liquids from resurfacing (rewetting) and contacting the wearer. It is believed, however, that a topsheet having the features described herein, for example, when combined with an appropriately composed and configured fluid management layer (for example as disclosed in in co-pending U.S. Prov. App. Ser. No. 63/256,164) can effectively prevent rewetting to a comparable degree, or better, than pads having topsheets comprising film across a predominant portion of topsheet x-y surface area. Without intending to be bound by theory, it is believed that the careful selection of the fiber types in each of the strata in the fluid management layer, and the linear densities of the fiber types, can result in a desired combination of suitably low fluid acquisition time, and low rewet, overcoming the typical tradeoff in these conflicting objectives associated with prior nonwoven topsheets. This performance is evident in a combination of the nonwoven topsheet and a fluid management layer described herein.

In addition to the features described herein, nonwoven web material used to form a topsheet may have any of the features, structures, components and/or compositions described in, for example, co-pending U.S. provisional application Ser. Nos. 63/256,164 and 63/316,097, the disclosures of which are incorporated herein by reference.

Basis Weight

The topsheet nonwoven may be manufactured to a basis weight of at least about 15 gsm, more preferably at least about 40 gsm, or most preferably at least about 60 gsm, specifically reciting all values within these ranges and any ranges created thereby. In some examples, a nonwoven topsheet contemplated herein may be manufactured to have a basis weight of about 15 gsm to 80 gsm, more preferably about 20 gsm to 60 gsm, or most preferably about 20 gsm to 40 gsm, specifically reciting all values within these ranges and any sub-ranges created thereby. In particular examples the topsheet nonwoven may be manufactured to a basis weight of about 18 gsm to 40 gsm, more preferably about 20 gsm to 30 gsm, even more preferably about 22 gsm to 26 gsm, specifically reciting all values within these ranges and any sub-ranges created thereby. The range of desirable basis weight is influenced, at the lower end of the range, by the need for a level of web tensile strength needed for processing, and by consumer preferences for a level of opacity and substantiality of loft, feel and appearance. The range of desirable basis weight is influenced, at the upper end of the range, by the need for suitably rapid fluid acquisition and passage of fluid through the topsheet, and material cost concerns.

Fiber Composition

Nonlimiting examples of constituent materials suitable for use in a topsheet nonwoven include fibrous materials made from natural fibers, e.g., cotton, including 100 percent organic cotton, modified natural fibers, semi-synthetic fibers (e.g., fibers spun from regenerated cellulose) synthetic fibers (e.g., fibers spun from polymer resin(s)), or combinations thereof. Synthetic fibers may include fibers spun from single polymers or blends of polymers. Synthetic fibers may include monocomponent fibers, bicomponent fibers or multicomponent fibers. (Herein, bi- or multicomponent fibers are fibers having cross sections divided into distinctly identifiable component sections each formed of a single polymer or single homogeneous polymer blend, distinct from that of the other section(s). Such fibers and processes for making them are known in the art. Examples of bicomponent fiber configurations with substantially round cross sections include side-by-side or "pie slice" configurations, eccentric sheath-core configurations and concentric sheath-core configurations.

Nonwoven topsheets contemplated herein may include fibers having myriad combinations of constituent components. For example, fibers may be spun from polymeric materials, such as polyethylene (PE) and/or polyethylene terephthalate (PET). Fibers may be spun in the form of bi-component fibers. In some examples, bi-component fibers may have a core component of a first polymer (for example, PET) in combination with another polymer as a sheath component, in a sheath-core bicomponent configuration. In more particular examples, PE may constitute the sheath component in combination with a PET core component. Fibers that include a PET component, having relatively greater stiffness and resilience, may be selected to help provide bulk and resilience and a resulting cushiony feel to the nonwoven web. Additionally, fibers that include a PET component, having comparatively greater resilience, help the web retain the area and dimensions of apertures created therethrough, if included.

Other polymeric materials may be included. For example, fibers spun of polypropylene, polyethylene, co-polyethylene terephthalate, co-polypropylene, and other thermoplastic resins may be included. It may be desired that the polymer with the lower melting temperature form the sheath component when sheath-core bi-component fibers are included. Additionally, without intending to be bound by theory, it is believed that the use of polyethylene terephthalate as a core component can help impart resilience to the topsheet.

Polyethylene, as a polymer component from which fibers may be spun, has a relatively lower melting temperature, and exhibits a relatively slick/silky surface feel as compared with other potentially useful polymers. PET has a relatively higher melting temperature, and exhibits relatively greater stiffness and resiliency. Accordingly, in some examples topsheet nonwoven fibers that are of a sheath-core bicomponent configuration may be desired, in which the sheath component is predominantly polyethylene and the core component is predominantly PET. The polyethylene is useful for imparting the fibers and thus the topsheet with a silky feel, and for enabling inter-fiber bonding via heat treatment that cause sheaths of adjacent/contacting fibers to melt and fuse at the lower melting temperature of the polyethylene, while the PET is useful for imparting resilience, and due to its higher melt temperature does not melt in a heat treatment process involving suitably controlled temperature(s). It is believed that a suitable weight ratio in such PE/PET sheath-core bicomponent fibers may be about 40:60 to about 60:40.

The constituent fibers may be staple fibers. The staple fibers may be carded, and consolidated to create a web having cohesiveness and tensile strength via a spunlacing process or other suitable process that integrates and/or entangles the fibers. In some examples the web may be calender bonded to impart additional consolidation and tensile strength. In other examples, however, calender bonding might be, preferably, foregone, because it can reduce web caliper and loft, reduce porosity, increase web stiffness, and adversely affect or reduce other softness attributes perceivable by consumers.

Surface Treatment (Hydrophilicity/Hydrophobicity)

Depending upon the chemical composition thereof, surfaces of fibers will be, inherently, either hydrophilic or hydrophobic. For example, surfaces of fibers spun or otherwise formed from some types of polymers such as polyethylene and polypropylene will be, inherently, hydrophobic. In contrast, surfaces of other types of fibers such as fibers spun from regenerated cellulose (e.g., rayon, viscose, lyocell, etc.) are inherently hydrophilic. Surfaces of natural fibers may be inherently hydrophilic or hydrophobic, but this may depend upon the processing the fibers have undergone. For example, cotton fibers as harvested bear coatings of natural waxes and as such their surfaces are hydrophobic. After they have undergone processes including scouring and bleaching, however, the waxes will have been stripped away, rendering the fiber surfaces hydrophilic.

Manufacturers and/or suppliers of spun synthetic staple fibers currently apply coatings, in the form of surface finishing agents or processing aids, to the fibers, for purposes of providing lubricity in, e.g., carding processes. These surface finishing agents or processing aids may be formulated to be either hydrophobic or hydrophilic, and substantially durable for purposes herein, in that they will not dissolve in aqueous fluids over the ordinary duration of wear of a pad. Thus, a manufacturer or supplier of spun synthetic staple fibers may offer fibers with either hydrophobic or hydrophilic surface finishes, and currently, several manufacturers in the nonwovens materials industry do this.

Noting that spun synthetic staple fibers may be obtained with either inherently hydrophobic, or inherently hydrophilic, surfaces, or obtained with surface finishes that render their surfaces hydrophilic or hydrophobic at the purchaser's option, it may be desirable to choose fibers with surfaces that are either hydrophilic ("hydrophilic fibers") or hydrophobic ("hydrophobic fibers"), or, to choose a blend of fibers of both types.

In some examples it may be preferable that the fiber constituents of the topsheet be, by weight, predominantly, substantially, or entirely hydrophobic, or rendered hydrophobic via fiber surface finish. A topsheet formed of a nonwoven web with predominantly hydrophobic fiber constituents will be resistant to rewetting. On the other hand, if the sizes of the pores or inter-fiber voids within the fibrous structure of such nonwoven web are not sufficiently large, the topsheet may resist the passage of fluid from the wearing facing surface through to the absorbent core components of the pad therebeneath, i.e., will not readily/rapidly acquire fluid, unless other features are included in combination, as described herein.

In other examples, fibers constituting portions, a majority (by surface area), or all, of the section of web material from which of the topsheet is formed, may be a blend of both hydrophobic fibers and hydrophilic fibers. In such examples, the hydrophilic fibers can serve to help wick fluid from the wearer-facing surface of the topsheet down to the absorbent core components beneath, while the hydrophobic fibers can serve to help the topsheet resist rewetting. It is believed that a successful balance may be struck for such examples.

Accordingly, in some examples the topsheet nonwoven may include a mix of hydrophobic and hydrophilic fibers. For example, the nonwoven may include at least about 40 percent, more preferably at least about 50 percent, or most preferably at least about 60 percent hydrophilic fibers by weight of the fibers, specifically including all values within these ranges and any ranges created thereby. In more particular examples, the nonwoven topsheet may comprise about 40 percent to 70 percent, more preferably about 45 percent to 68 percent, or most preferably from about 50 percent to 65 percent, by weight, hydrophilic fibers, specifically reciting all values within these ranges and any ranges created thereby. The topsheet nonwoven may include a blend of hydrophilic fibers and hydrophobic fibers in a weight ratio of hydrophilic fibers to hydrophobic fibers of 30:70 to 70:30, more preferably 35:65 to 65:35, and even more preferably 40:60 to 60:40. As noted above, the hydrophilicity of the hydrophilic fibers may be effected by application of a surface treatment composition.

Without intending to be bound by theory, it is believed that where a majority of the fibers are hydrophilic, fluid acquisition speed can be improved by combination with other features described herein, while not overly impacting rewet in a negative or unacceptably negative manner. Where less rewet is the goal, then the converse may be true. In this circumstance, a higher weight fraction of hydrophobic fibers may be desired.

Linear Density

Fibers are typically manufactured, selected and purchased by linear density specification, expressed as denier or decitex. For fibers of a given polymer constitution, linear density correlates with fiber size/diameter.

In some examples, the fibers constituting the topsheet may selected to have an average linear density of about 1.0 to 5.0 denier, more preferably about 1.5 to 4.5 denier. All combinations of sub-ranges within these ranges are contemplated herein. Fiber constituents of topsheet material having a denier proximate the lower end of these ranges, being relatively more fine, tend to impart relatively greater softness of feel to the topsheet material, but also smaller pore (interstitial space) size and therefore lower fluid permeability. On the other hand, fiber constituents having a denier proximate the higher end of these ranges, being relatively more coarse, tend to impart relatively greater stiffness, but also larger pore size and therefore greater fluid permeability. With greater fluid permeability, the designer may have greater freedom to manufacture the topsheet with a greater proportion of hydrophobic fibers, which may provide greater resistance to rewetting. However, imparting greater pore size may also have the effect of imparting less opacity, which may otherwise be valued for purposes of obscuring staining of the materials in the absorbent structure 302. The designer may wish to balance these features when selecting fiber denier. The selection may also be influenced by the number and size of apertures created in the topsheet, as described herein.

Without intending to be bound by theory, it is believed that, for a nonwoven of particular selected basis weight as contemplated herein, inclusion of fibers having a linear density greater than about 5.0 denier may result in a topsheet that lacks, for some consumers, a sufficiently soft feel, since such relatively larger fibers would tend to be stiffer. Conversely, a selection of fibers having a linear density less than about 1.0 denier result in unduly small interstitial spaces/voids between and among the fibers, and make fluid acquisition and movement through the topsheet unacceptably difficult unless apertures are included. In any event, a suitable pattern of apertures may be imparted to the topsheet, to increase liquid permeability and thereby offset the effects of inclusion of relatively smaller denier fibers.

Staple Fiber Length

Suitable fibers may be staple fibers having a length of at least about 30 mm, 40 mm, or 50 mm, up to about 55 mm, or about 30 to 55 mm, or about 35 to 52 mm, reciting for said range every 1 mm increment therein. In particular example, staple fibers may have a length of about 38 mm.

Apertures

It is believed that, in topsheet nonwovens that are formed of fibers of relatively small size/linear density and/or fibers that are predominantly, substantially or entirely hydrophobic, acquisition speed may be substantially increased by forming a pattern of apertures through the web. Generally, the preferred apertures will have sizes that are substantially larger than the average pore/void size (size of inter-fiber spaces) within the nonwoven web.

Figure 11:
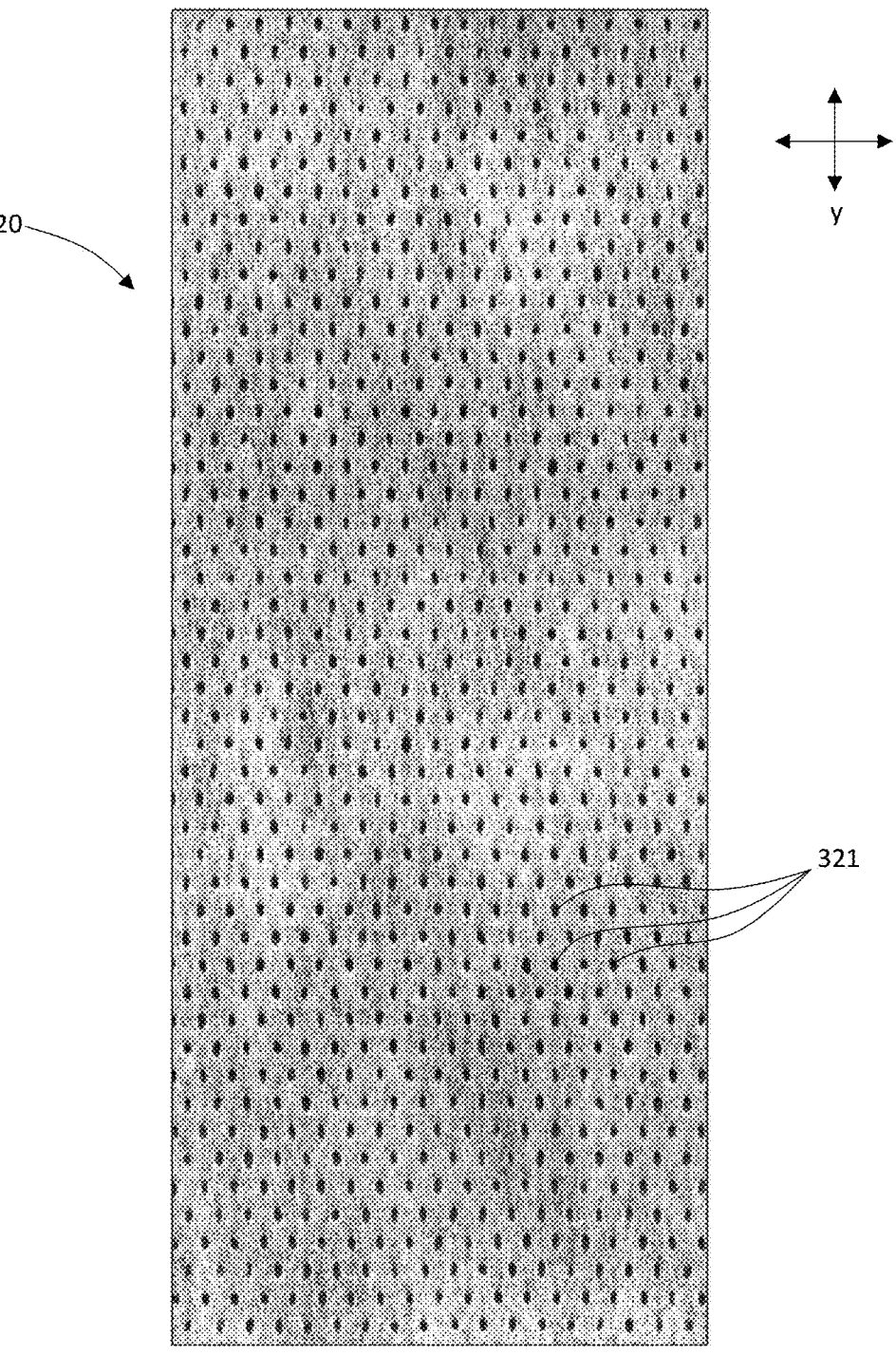
FIG. 11 is a plan view (along a z-direction) image of a portion of a nonwoven web material having a pattern of apertures therethrough.
Figure 12:
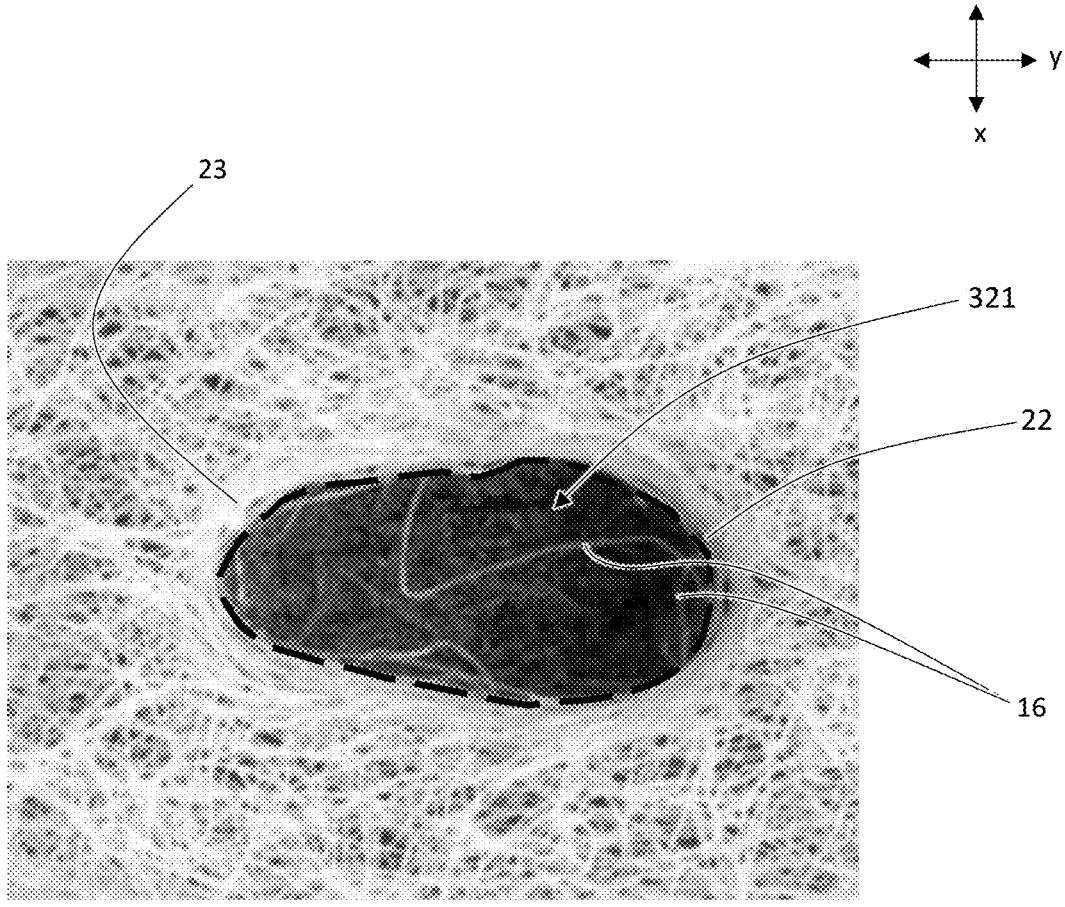
FIG. 12 is a plan view (along a z-direction) magnified image of a portion of a nonwoven web material having an aperture therethrough.

An example of a section of apertured topsheet nonwoven web material 20 having a pattern of apertures 321 therethrough is depicted in FIG. 11. A magnified image of example an aperture through a nonwoven web material is depicted in FIG. 12. Apertures are distinguishable from randomly-disposed pores or voids through the nonwoven web material, in that they are created by readily discernible displacements of fibers and/or fiber component material, along x-y directions, resulting in concentrated groups of densified material and/or displaced fibers that define the perimeter 22 of a z-direction hole/opening through the nonwoven web that is relatively substantially larger than the randomly distributed pores or voids between and among the fibers constituting the nonwoven material. Apertures may be created through the web via any suitable process and equipment known in the art. In some examples, however, apertures may be created through a web via a process and equipment described herein and configured to impart the average x-y dimension aperture areas specified in the enumerated examples herein. Herein, the x-y dimension area of an aperture is defined by visually discernible inside edges of the densified zone 23 about the perimeter 22 of the aperture. Stray individual fibers that may have escaped the main structure and/or the densified zone about the perimeter, and cross into or through the main open area of the aperture (by way of illustrative example, stray individual fibers 16 shown in FIG. 12) are not considered subtractive from the aperture area for purposes herein. Further, without intending to be bound by theory, it is believed that the where the shapes of the apertures are too oblong or narrow, fluid acquisition speed may be negatively impacted. Accordingly, it may be desired that the apertures have a limited maximum average x-y direction aspect ratio (greatest dimension:smallest dimension in x-y directions). Thus, it may be desired that the average aspect ratio of the apertures be about 2.5:1 to 1:2.5; more preferably 2:1 to 1:2; even more preferably from 1.5:1 to 1:1.5, still more preferably from 1.3:1 to 1:1.3, and most preferably from 1.2:1 to 1:1.2; all combinations of subranges within these ranges are contemplated herein. Further, it is preferable for purposes of retaining structural integrity of the web and shape integrity of the apertures, that the x-y plane shapes of the majority or all of the apertures in, at least, the central region 305 (see FIG. 1) if not the majority or entirety of the topsheet, be fundamentally rounded shapes (e.g., circular, oval, ovoid, elliptical, stadium, etc.), having no defined sharp corners. Accordingly, it may be desired that the pins on the roller used to create the apertures have radially outermost acting surfaces having shapes that do not define sharp corners, when viewed along a radially inward direction toward the axis of the roller.

Central Region Aperture Arrangement

Collectively, the x-y plane areas within the perimeters of all of the apertures in the portion of interest of the topsheet amount to an aggregate open x-y plane area ("open area") in the topsheet nonwoven. In combination with a desired average aperture size, a desired open area for the central region 305 has been identified, in order to effectively mitigate potential obstacles to fluid acquisition that may result from constitution of fibers of finer denier and/or fibers that are predominantly hydrophobic. Accordingly, it may be desired that a first arrangement of apertures 322 constitutes a Percent Open Area, within central region 305, of 1 percent to 12 percent, more preferably 2 percent to 10 percent, and even more preferably 3 percent to 8 percent; all combinations of subranges within these ranges are contemplated herein. It is preferred that such amount of open area be present in the central region 305. The lower limits of these ranges are imposed by the need for efficacy/performance; the apertures should provide at least a minimum amount of open area in order to be effective as may be included for the purposes described herein. The upper limits of these ranges are imposed by the need for consumer acceptance; if the open area is too great, consumers may perceive that the topsheet is fragile or of poor quality; and further, the topsheet becomes less effective at retaining fluid therebeneath, and insufficiently effective at reducing visibility of staining of underlying absorbent components, by absorbed fluid present therein.

Referring to FIG. 1, for purposes contemplated herein, central region 305 is a rectangular section of the topsheet that is 80 mm long in the longitudinal direction and 20 mm wide in the lateral direction. It is centered about the longitudinal axis 400. It straddles the lateral axis 500 and may be centered thereabout, or may be centered about a lateral line located forward of the lateral axis (i.e., toward the front of the pad). The Percent Open Area of central region 305 is the fraction (expressed as a percentage) of the x-y area therewithin that is open therethrough in the z-direction, by the collective presence of the apertures therewithin. Expressed differently, the Percent Open Area within the ROI is the total open x-y area of the apertures within the central region, divided by 1,600 mm$^2$, times 100%.

The percent fraction open area in the central region 305 may be obtained in some examples from the specifications given to or provided by the manufacturer of the topsheet nonwoven web material. Where this is unavailable, it may be measured via any suitable measurement technique that may be applied, in a manner consistent with the description of the x-y dimension area of an aperture area and description of "open area," above, which may include but is not limited to the Apertures Percent Open Area Measurement Method set forth below.

Further, in combination with the open area percentages described above, and for similar reasons, it may be preferred that the first arrangement of apertures 322 within central region 305 have an average size of 0.2 mm$^2$ to 0.75 mm$^2$, more preferably 0.4 mm$^2$ to 0.60 mm$^2$; all combinations of subranges within these ranges are contemplated herein.

Outboard Aperture Arrangement

Laterally and/or longitudinally outboard from central region 305, movement of discharged fluid through the topsheet 301 is less of a concern, since these areas are not ordinarily as proximate the source and location of fluid discharge when the pad is suitably placed for wear/use. It has been learned, however, that one or more additional arrangements of paths of apertures outboard of the central region as described herein may have beneficial effects. Referring to FIG. 1, one or more second arrangements of apertures 323 may be created in topsheet 301 and located laterally and/or longitudinally outboard of central region 305.

In some examples it may be preferred that the apertures 324b forming these second arrangements have an average size smaller than the apertures of the first arrangement 322. In some examples it may be preferred that apertures 325b have an average size in the range of 0.2 mm$^2$ to 0.75 mm$^2$; all combinations of subranges within this range are contemplated herein.

Alternatively or in addition, in some examples it may be preferred that the apertures 324b be arranged in one or more paths of apertures, as defined herein. Paths of such relatively smaller apertures, preferably two or more paths arranged together as suggested in FIG. 1, can create both an actual and visual effect for the wearer, of a barrier structure that can serve to prevent fluid from migrating across the topsheet to locations outboard of the paths, as well as a supplemental group of passages through the topsheet down to underlying absorbent components to reduce the likelihood that fluid will migrate across/along the wearer-facing surface of the topsheet in x-y directions and escape the pad. Additionally, such paths can impart the pad and topsheet with a pillowy visual appearance that wearers may perceive as enhancing softness.

From FIG. 1 it will be noted that first 322 and second 323 arrangements of apertures may be "pitched," i.e., discrete and unitized, for each pad, rather than being part of a regular pattern that is continuous with and undifferentiated from pad to pad. This characteristic is incidental to the first and second arrangements as described above, and depicted by way of non-limiting, illustrative example in FIG. 1.

Figure 2B:
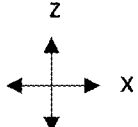
FIG. 2B is a schematic lateral cross section of one possible alternative non-limiting example of the feminine hygiene pad of FIG. 1, taken through line 2-2 in FIG. 1.
Figure 2B:
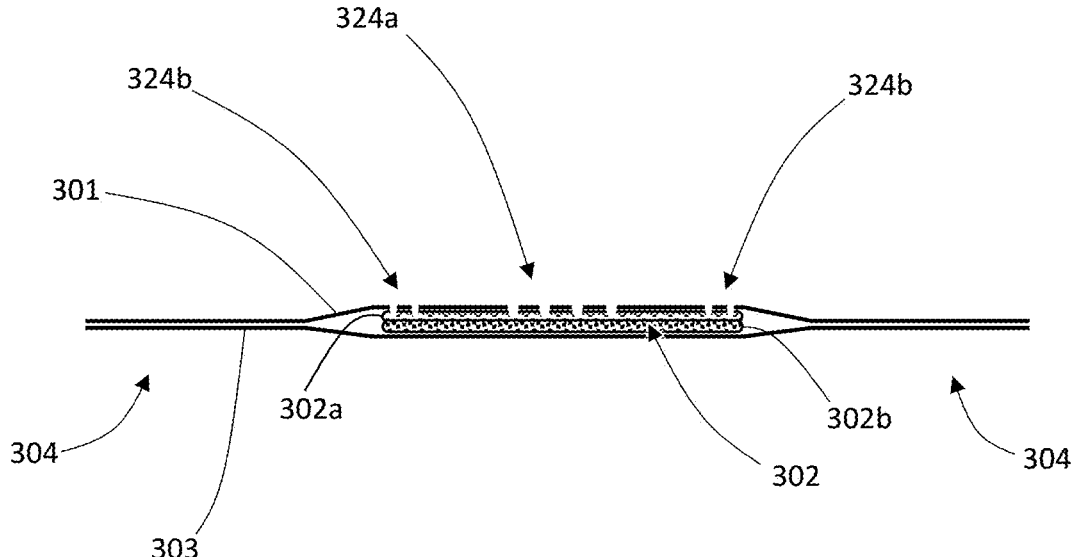
Figure 3:
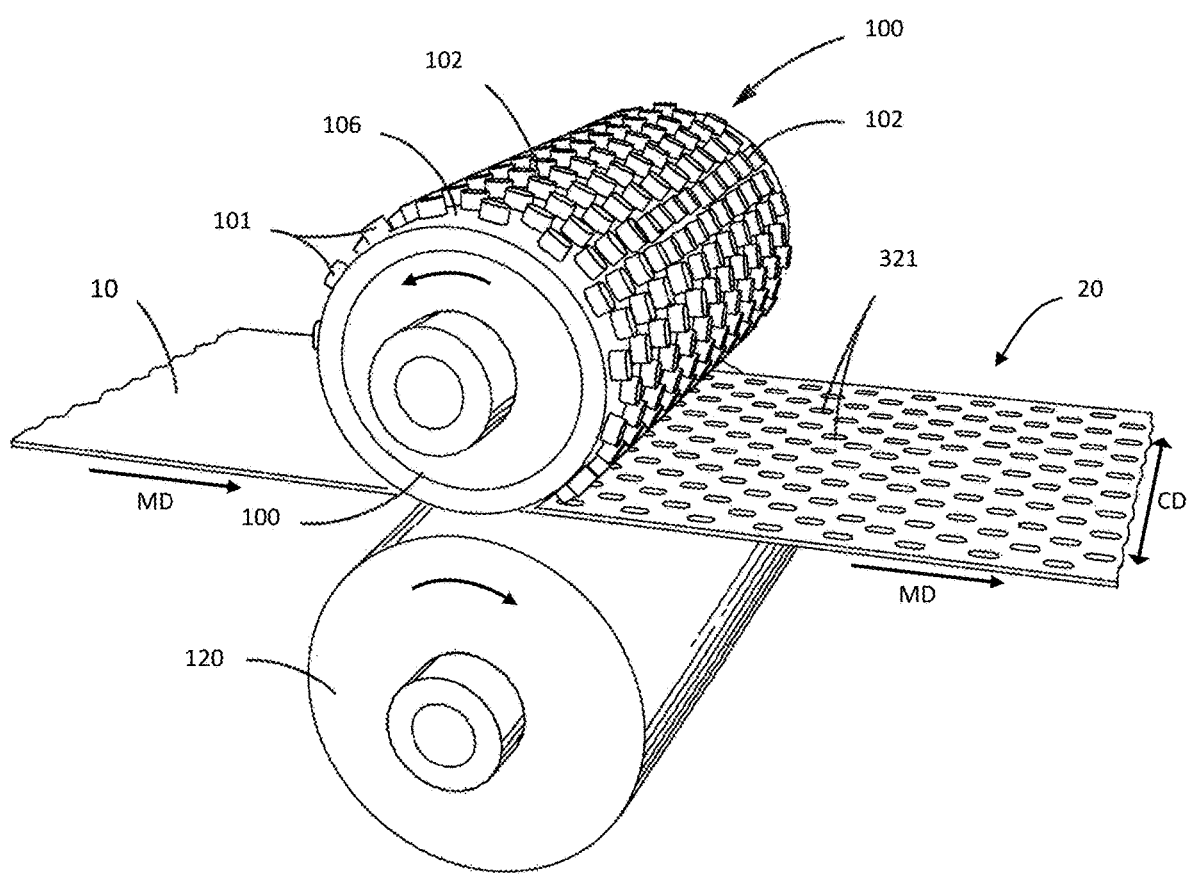
FIG. 3 is a schematic perspective depiction of a pair of aperturing rollers in operation upon a nonwoven web.
Figure 15:
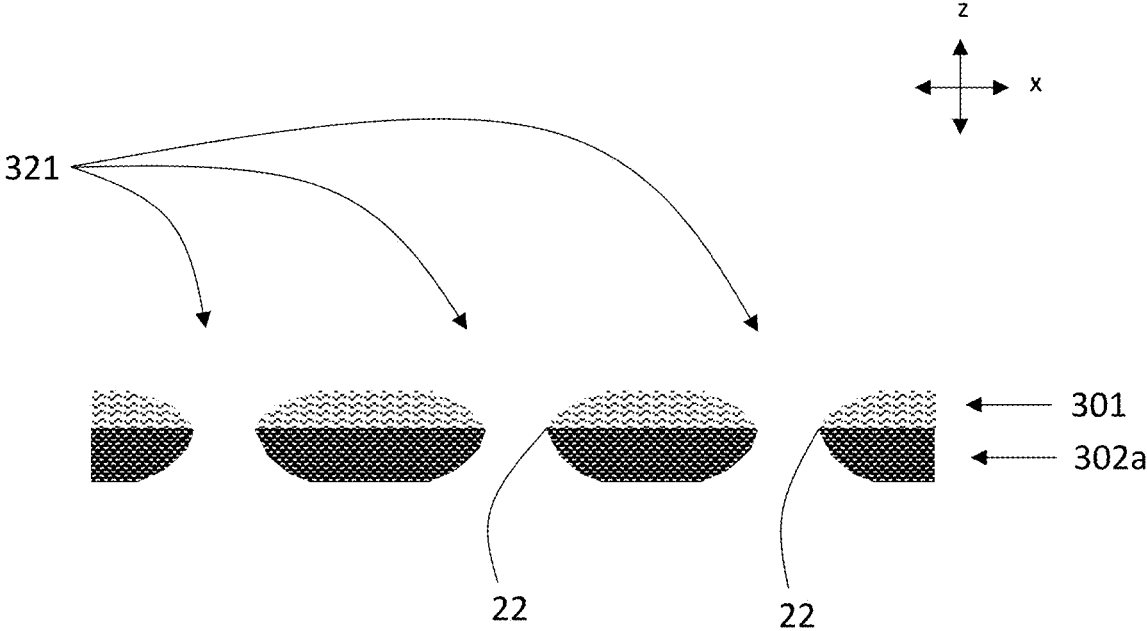
FIG. 15 is a schematic expanded z-direction cross section of a combination of a topsheet and fluid management layer having apertures formed through the combination.

Referring to FIGS. 2B and 15, in some examples, apertures 321 through a topsheet 301 material may be formed simultaneously and in substantial z-direction alignment and x-y direction size correspondence, with apertures through an immediately subjacent layer component such as fluid management layer 302a, by, for example, conveying both materials simultaneously through a pair of aperturing rollers 100, 120 (e.g., FIG. 3), as described herein. This may have the effect not only of creating and/or enhancing a pillowy appearance proximate the location(s) of such apertures, e.g., proximate the central region and/or periphery of the absorbent structure 302, but also providing a plurality of direct pathways for fluid to move along a z-direction downward to a storage layer 302b (see FIG. 2B). In the aperturing process, some partial bonding may be effected about the perimeters 22 of the apertures 321, among and between fibers of the topsheet nonwoven material and fibers of the fluid management layer nonwoven material, resulting in approximately funnel-shaped z-direction depressions in the topsheet circumscribing the apertures. This imparts topography or surface contours along the topsheet, further enhancing a pillowy visual appearance.

Bonding

Figure 13:
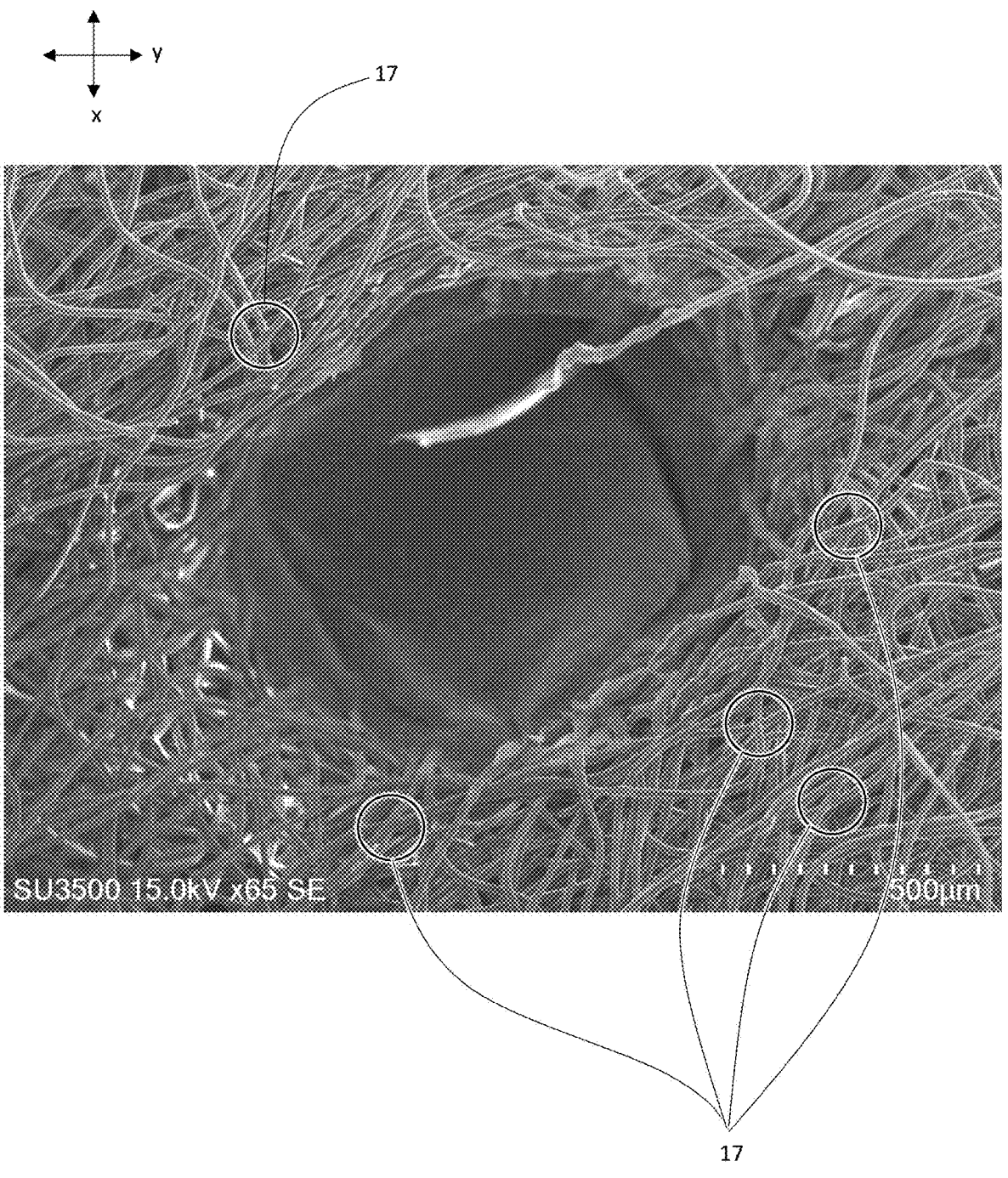
FIG. 13 is a plan view (along a z-direction) magnified image of a portion of a nonwoven web material having an aperture therethrough.

In some examples, it may be desirable that the fibers forming the topsheet nonwoven be bonded following the carding/fiber laydown process, to impart a fabric-like structure and tensile strength (in both the MD and the CD) needed for the web to substantially retain its structure in downstream/later processes, and in the form of a topsheet, during use by a user/wearer. As an alternative to other methods of bonding such as mechanical compression spot bonding (e.g., calender bonding) (with or without application of heating energy), adhesive bonding, etc., it has been found that bonding via air-through heating is effective for creating fiber-to-fiber bonds and imparting structural integrity to the web, while preserving inter-fiber pore/void size and loft, and imparting resiliency, to the nonwoven. In examples of suitable processes, air heated to the selected heating temperature is blown and/or drawn (via vacuum) through the carded fiber web as it is conveyed on a carrier belt along a machine direction, through an oven or heating chamber. When operating parameters including heating air temperature and velocity, and exposure time, are appropriately adjusted, a plurality of randomly distributed fiber-to-fiber bonds may be created within the fiber network, which impart structural integrity to the web. Examples of such fiber-to-fiber bonds 17 may be seen in FIG. 13. When constituent fibers are, for example, sheath-core bicomponent fibers in which the sheath component is a polymer having a melting temperature lower than that of the core component, the process may be configured such that fusion bonds form between sheaths of adjacent contacting fibers without complete melting and loss of structure of the sheaths, while the cores remain in place, un-melted. In such process, the bonds may be formed without application of z-direction compression or effects thereof, and thus, without associated loss of caliper of the web and reduction in size of the inter-fiber pores/voids.

Aperturing Process, Resulting Features and Materials Selection

Referring to FIGS. 3 through 6B, generally cylindrical aperturing rollers, including aperturing roller 100 and opposing roller 120, operating upon a portion of a nonwoven web material are schematically depicted. Precursor web material 10 may be conveyed from an upstream supply 200, along a machine direction MD into a nip 110 between aperturing roller 100 and opposing roller 120, one or both of which are driven to rotate about axes that are parallel with each other and with a cross direction. An apertured nonwoven web material 20 exits the nip 110, have imparted therein an arrangement of apertures 321 of desired size, shape and configuration (as illustrated, in a nonlimiting example, in FIG. 11).

Aperturing roller 100 may have formed thereon and thereabout an arrangement of individual aperturing pins 101, which project radially outwardly from a base surface 106 of roller 100. Aperturing pins 101 have top surfaces 102 with surface areas that lie along an imaginary cylindrical shape. The top surface 102 of an aperturing pin 101 is, preferably, smooth and polished, with substantially no macroscopic cavities or irregularities therein. The areas of top surfaces 102 are defined and delimited by top surface perimeter edges 103. Preferably, at least following manufacturing of the roller, prior to wear of the pins from use thereof, top surface perimeter edge 103 is defined by an angular, not rounded, transition away from top surface 102. A small chamfer 103a about the top surface perimeter edge 103 may be included, as suggested in FIGS. 6A and 6B, to reduce stress concentration at the edge and chances of fracture thereabout. However, top surface perimeter edge 103 is not substantially radiused or rounded at the transition away from top surface 102. (The reason for this is explained below.) For purposes of mechanical structural integrity of the pin 101, preferably, pin base perimeter 105 will circumscribe a larger surface area at the base of the pin than that of top surface 102, and pin wall(s) 104 will taper inwardly towards each other from pin base perimeter 105 to pin top surface perimeter 103. In this regard, angle α between top surface 102 and pin wall(s) 104 will preferably be greater than 90 degrees. The pin may be concavely radiused or rounded about base perimeter 105, to reduce localized stress at the pin base perimeter during use of the roller.

Top surfaces 102 of aperturing pins 101 may be imparted with any desired shape(s) and size(s), generally corresponding with the desired x-y direction shape(s) and size(s) of the apertures to be formed in the subject nonwoven web material. Similarly, the aperturing pins 101 may be arranged on aperturing roller 100 in any desired pattern, generally corresponding to the desired x-y direction pattern of apertures to be formed in the subject nonwoven material.

For purposes of structural integrity, preferably, the aperturing pins 101 and portion of the aperturing roller forming the base surface 106 thereof are integral, formed of the same, contiguous mass of material. A predominant portion if not the entire aperturing roller may be integrally formed of the same, contiguous mass of material. Preferably the material of which pins 101 and base surface 106 are formed will be relatively hard and rigid, such as a suitable steel or alloy thereof. In some examples, pins 101 or at least top surfaces 102 may be imparted with a suitably selected non-stick or stick-resistant coating to avoid or reduce sticking of material to be melted and/or deformed in the nip.

In some examples, aperturing pins 101 may be formed by machining away or otherwise removing material from a solid cylindrical body, leaving behind material that defines and constitutes pins 101.

Figures 4, 5A, 5B:
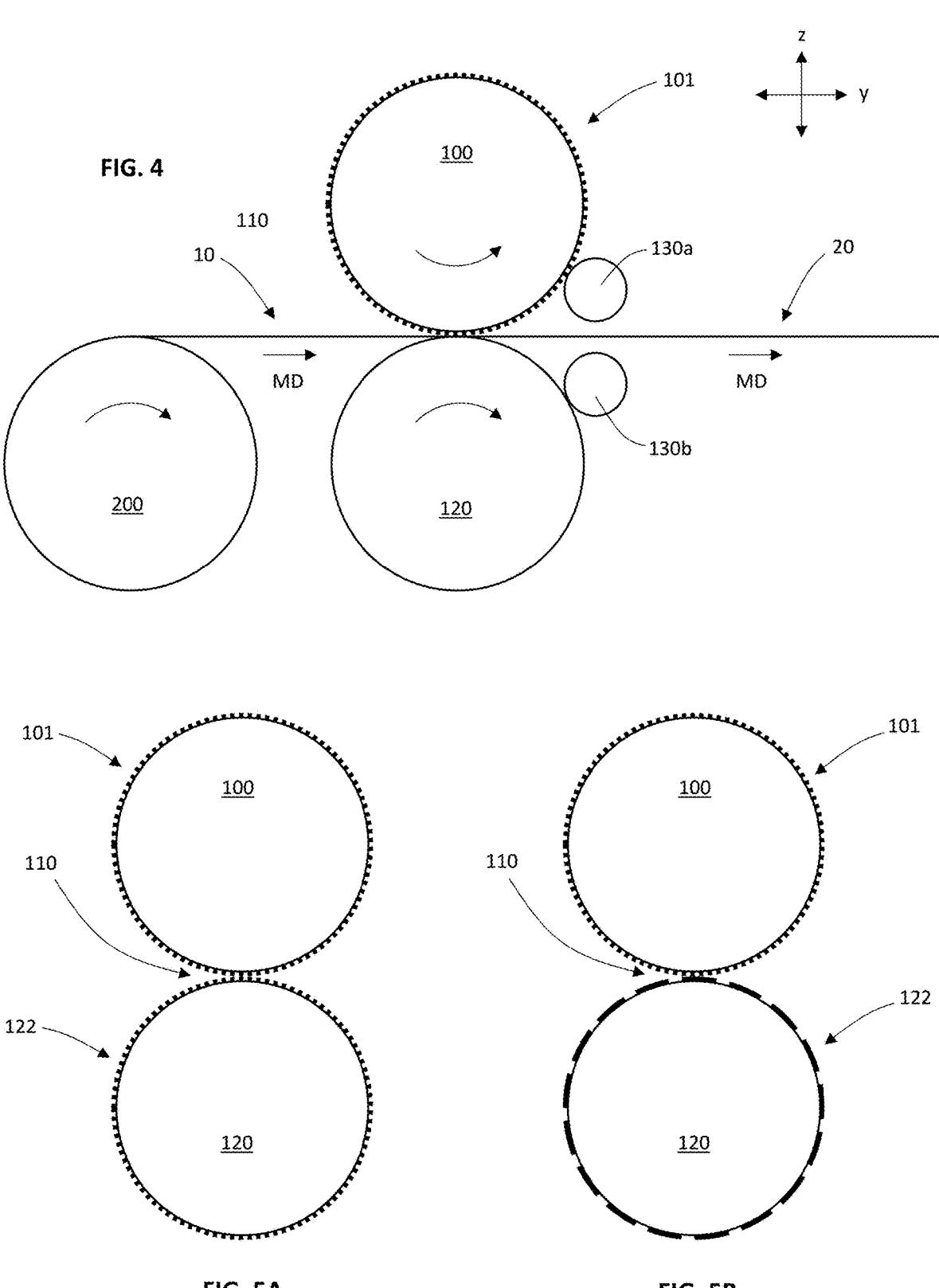
FIG. 4 is a schematic side view depiction of equipment on a manufacturing line including a pair of aperturing rollers in operation upon a nonwoven web.
FIGS. 5A and 5B are schematic side view depictions of differing alternative non-limiting examples of pairs of aperturing rollers.
Figures 6A, 6B:
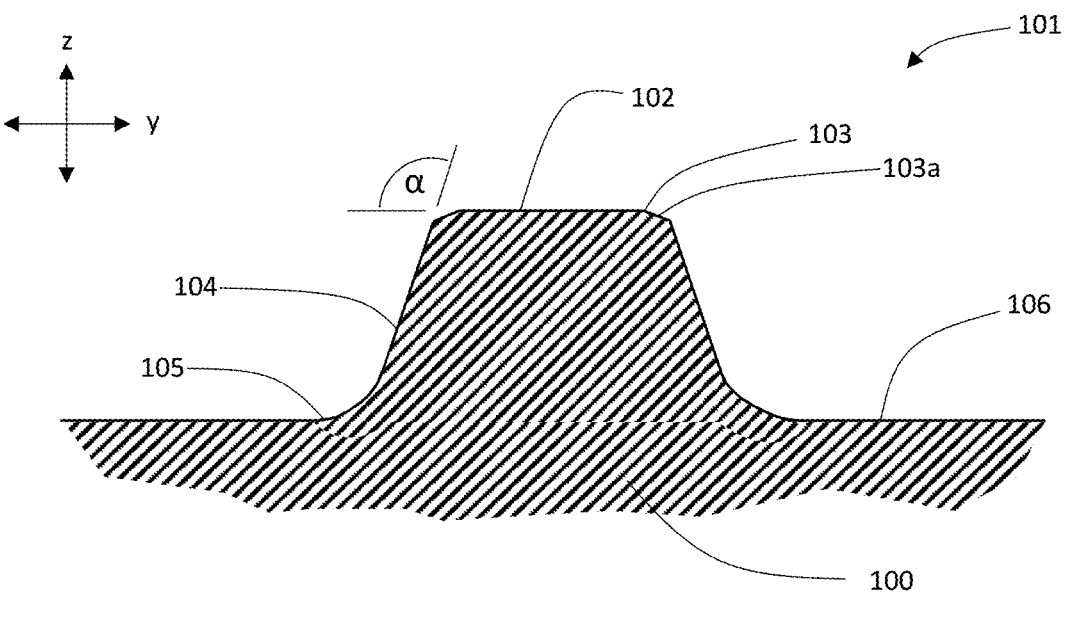
FIGS. 6A and 6B are respective schematic mid-section, and perspective, views of an example of an aperturing pin.

In some examples, as suggested in FIG. 4 opposing roller 120 may have a simple cylindrical outer surface that will meet all top surfaces 102 of aperturing pins 101 in the nip 110 between the rollers 100, 120. In other examples, opposing roller 120 may have thereon a formation of opposing structures 122 that effectively mirror, and meet the top surfaces 102, of aperturing pins 101 on aperturing roller 100, as suggested in FIG. 5A. In still other examples, as suggested in FIG. 5B, opposing roller 120 may have thereon a formation and arrangement of opposing structures 122 that are configured and arranged to meet desired subgrouping(s), but not all, of top surfaces 102 of aperturing pins 101 in the nip 110. In these latter examples, flexibility in providing a variety of selected differing configurations or patterns of apertures may be afforded, through manufacture and selected use of differing opposing rollers to be operated together with aperturing roller 100. Where only selective region aperturing of a nonwoven material is desired, these latter configurations may also enable extension of the useful life of the aperturing roller 100, since not all aperturing pins 101 need be utilized at the same time.

As with aperturing roller 100 and aperturing pins 101, it is preferred that material forming the surface(s) of opposing roller 120 and/or any opposing structures 122 thereof be relatively hard and rigid. These surfaces, also, may be imparted with a suitable selected non-stick or stick-resistant coating.

Figure 7:
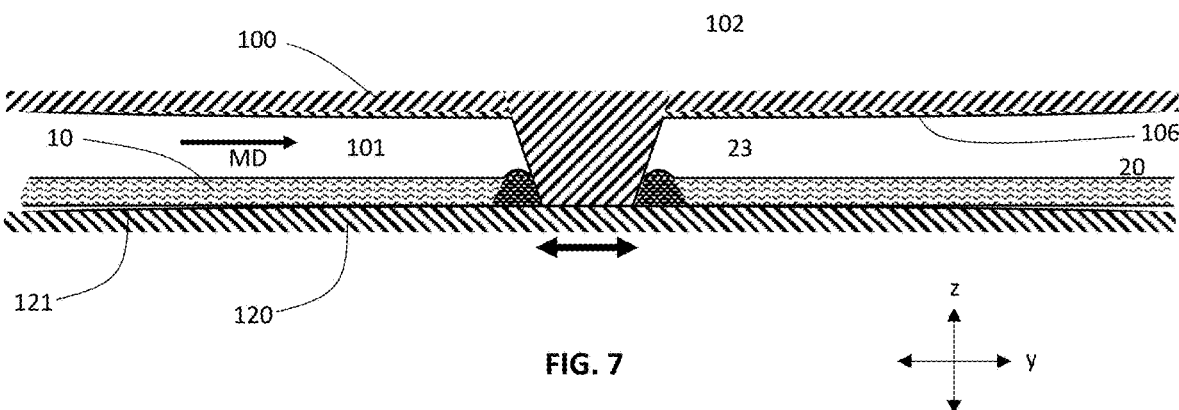
FIG. 7 is a schematic magnified cross-section (taken along a y-z plane) depiction of an aperturing pin operating on a portion of a nonwoven web in a nip between aperturing rollers.
Figure 8:
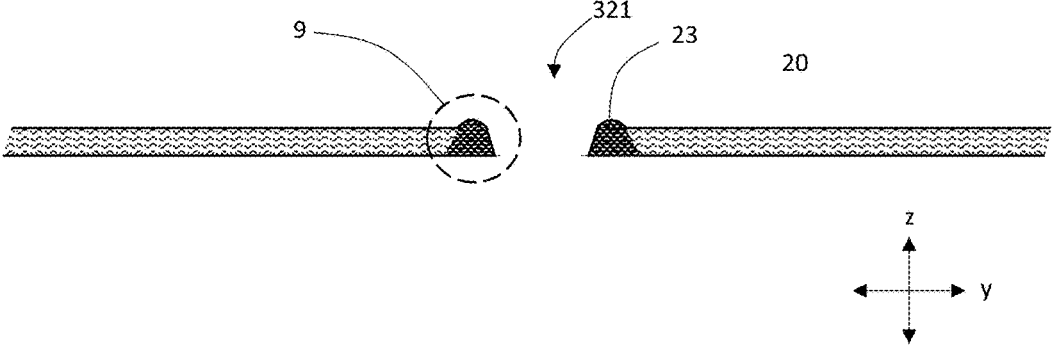
FIG. 8 is a schematic magnified cross-section (taken along a y-z plane) depiction of a portion of a nonwoven web having an aperture therethrough.
Figure 9:
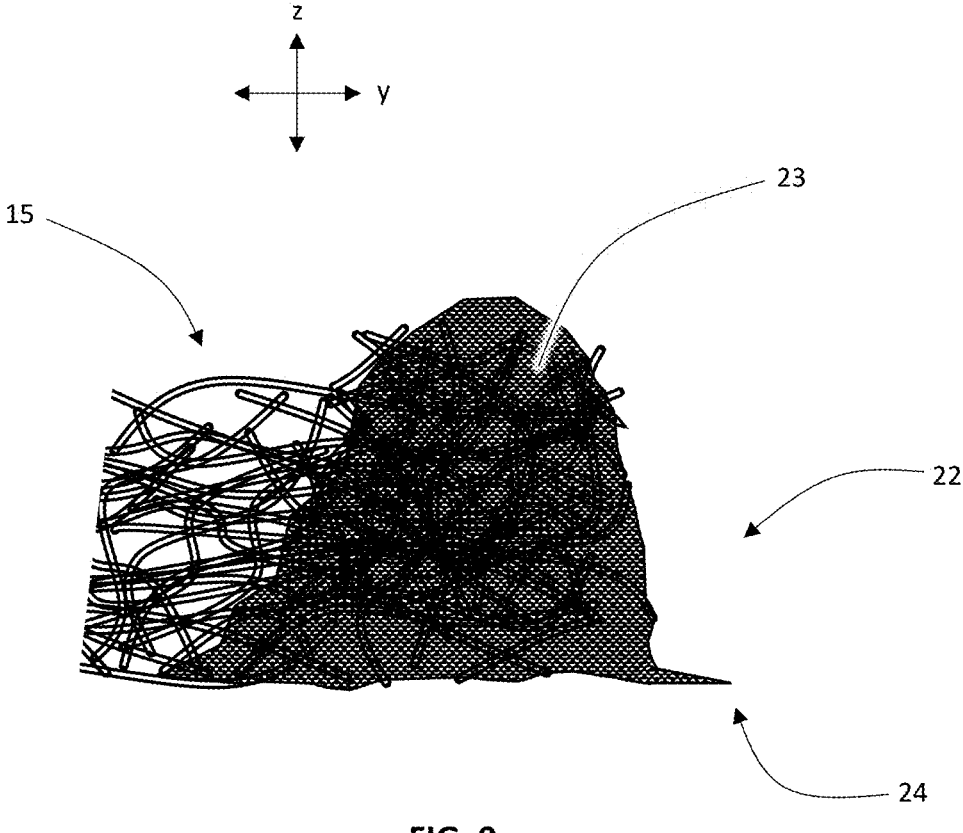
FIG. 9 is a schematic further magnified cross-section (taken along a y-z plane) depiction of the portion of the nonwoven web shown within circle 9 shown in FIG. 8.
Figure 10A:
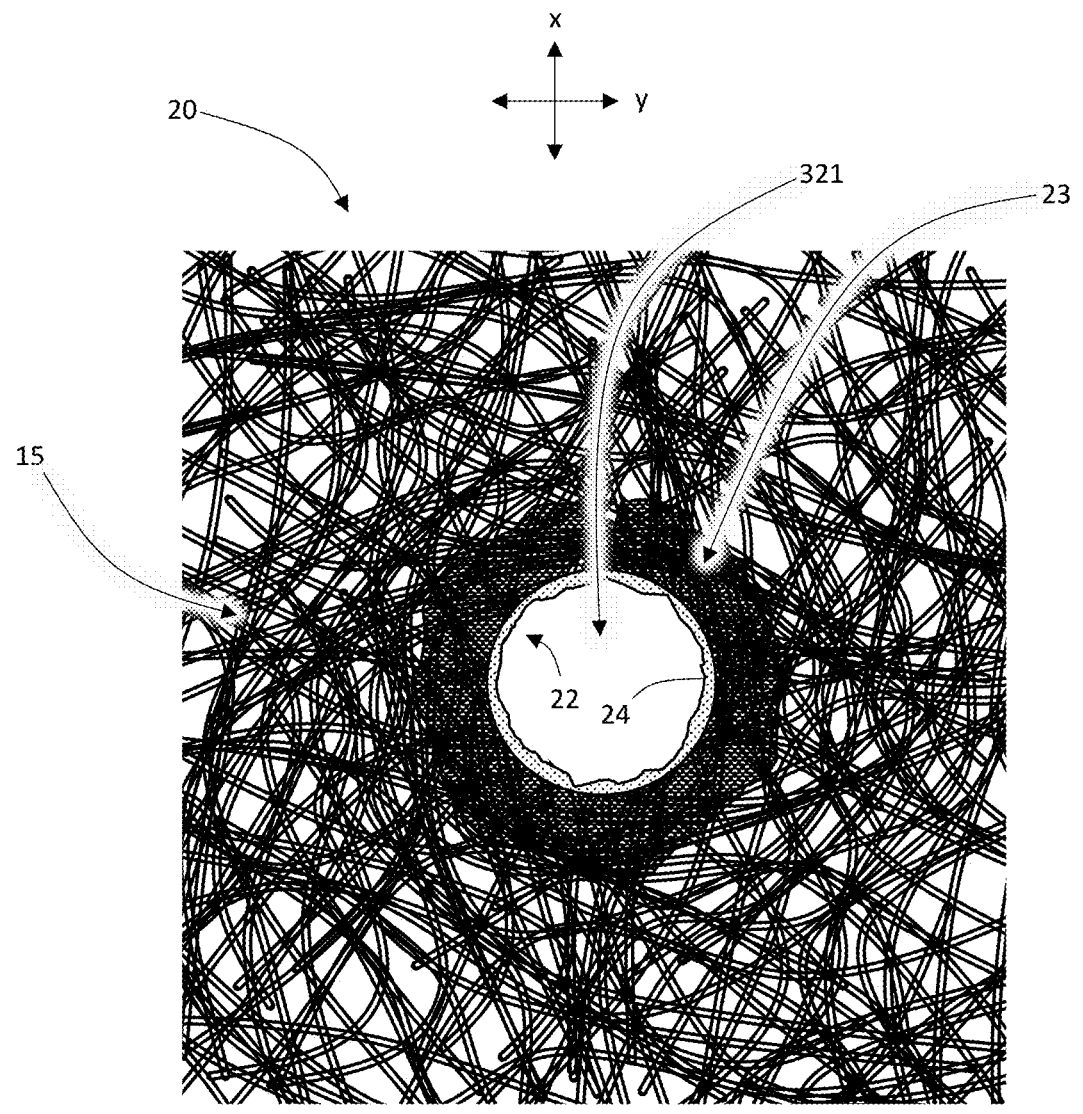
FIG. 10A is a schematic magnified plan view (along a z-direction) depiction of a portion of the nonwoven web including an aperture.
Figure 10B:
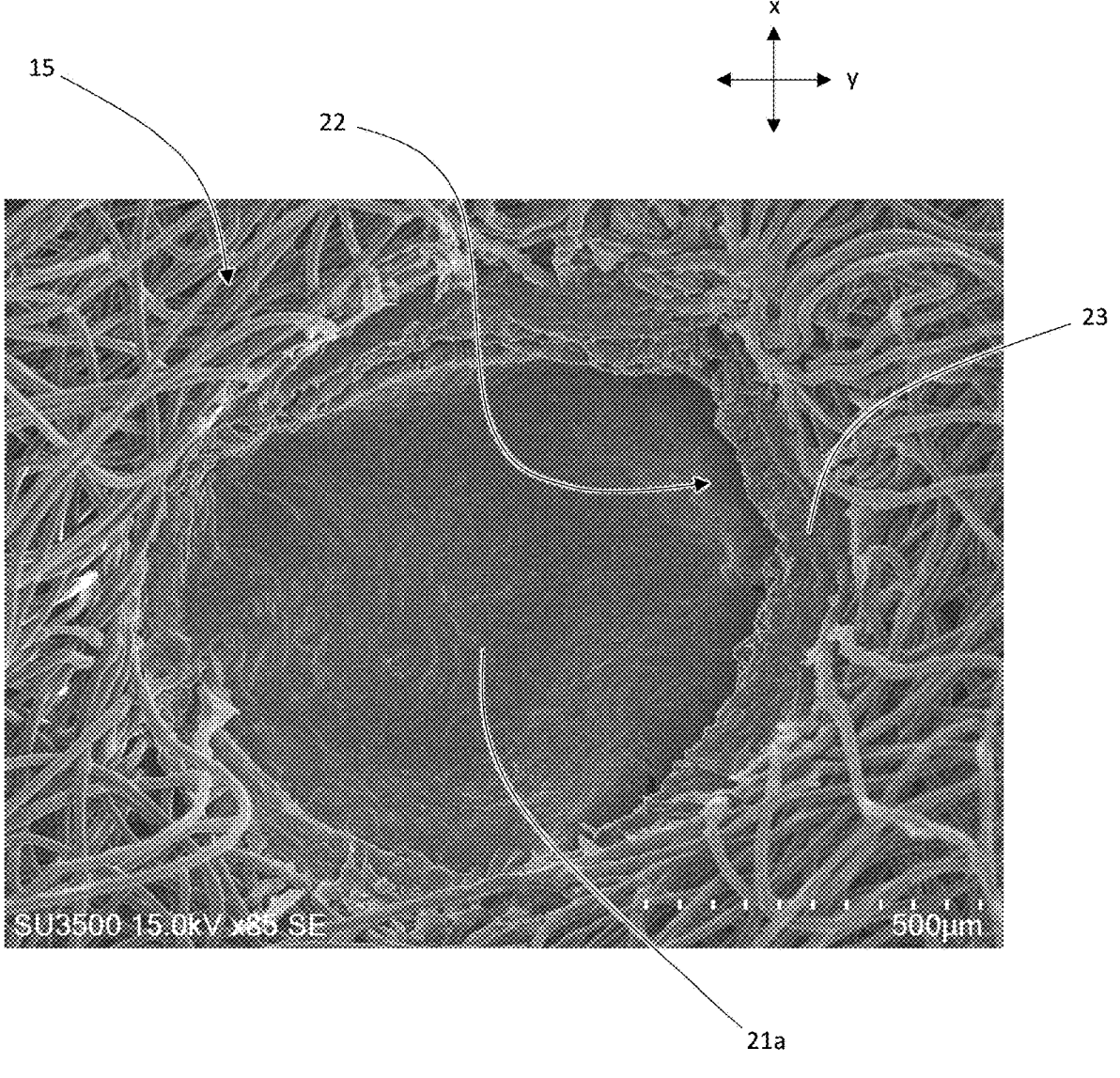
FIG. 10B is a magnified photograph of a portion of a nonwoven web following its exit from a nip between an aperturing roller and an opposing roller.
Figure 10C:
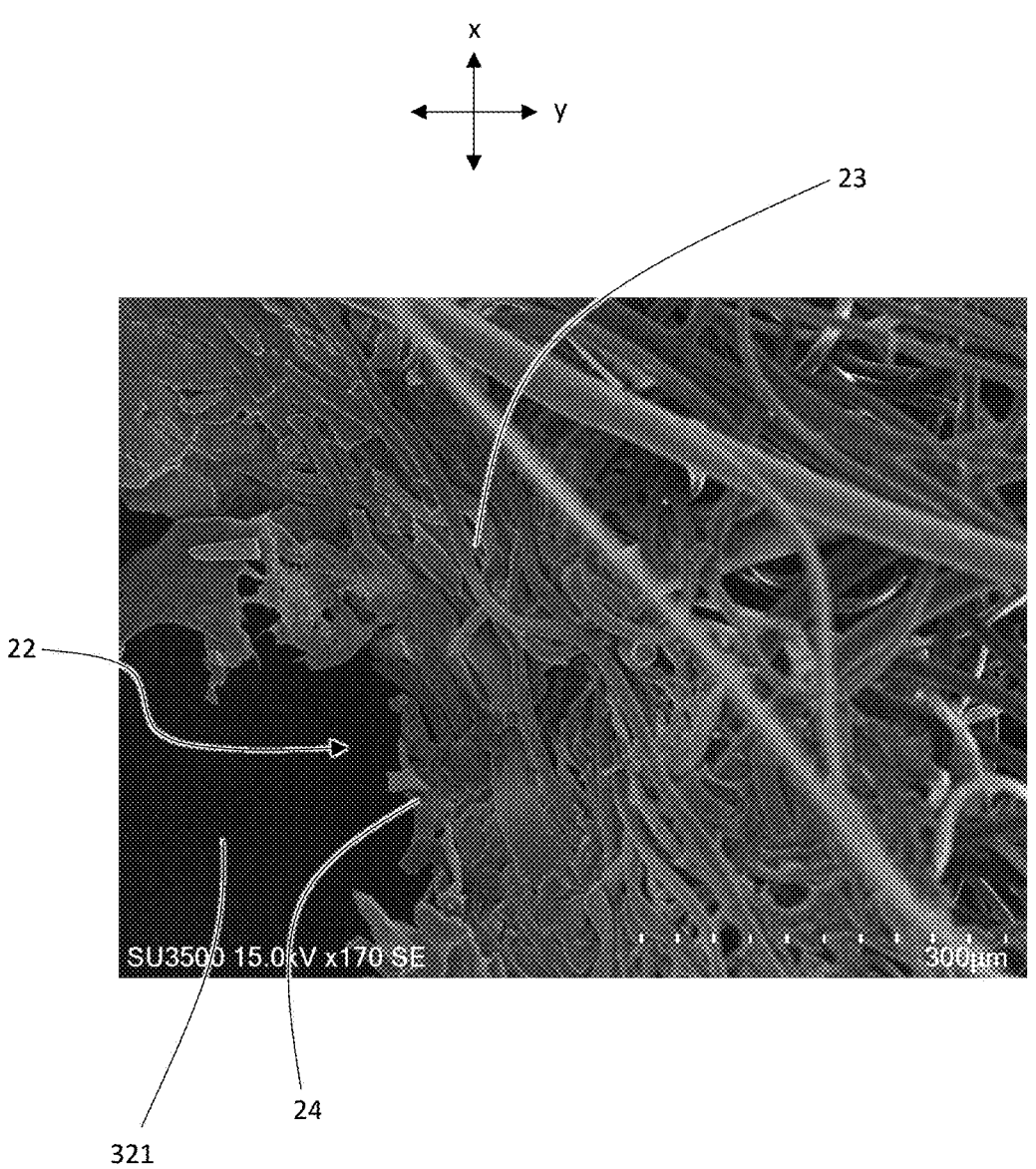
FIG. 10C is a further magnified photograph of a portion of a nonwoven web following its exit from a nip between an aperturing roller and an opposing roller.

When configured for operation, aperturing roller 100 and opposing roller 120 are preferably arranged so that there is substantially or effectively no (zero) specified clearance in the nip 110, between the top surfaces 102 of the aperturing pins 101, and the opposing surface(s) of the opposing roller 120. Referring to FIG. 7, with such configuration, polymer material forming constituent fibers of a precursor nonwoven web material will be plastically deformed and expressed from the nipping regions between the top surfaces 102 of the aperturing pins and the opposing roller surface(s), as suggested by the double-headed arrow in FIG. 7, out to a zone beginning at and extending in an x-y direction beyond the perimeter edges 103 of top surfaces 102 of pins 101. Referring to FIGS. 7-10C, a densified aperture perimeter zone 23 results. Depending upon the composition(s) of the nonwoven fiber 15 constituents and the operating temperatures of the rollers, densified zone 23 may include densified polymer material that has been melted and then fused, unmelted but plasticly deformed and expressed fiber components, or a combination thereof. The formation of a densified zone 23 defining the aperture 321 stabilizes the size and shape of the aperture within the apertured nonwoven web 20.

Either or both of aperturing roller 100 and opposing roller 120 may be heated to a temperature at or above the melt temperature of one or more of the polymer components of web fiber constituents, to facilitate such deformation and/or melting and fusing.

Even when the rollers are configured with substantially or effectively zero specified clearance in the nip 110, it may be difficult to cause expression of the entirely of the fiber component material(s) caught in the nipping regions between the pin top surfaces 102 and the opposing roller surface(s) 121. This can be the result of microscopic surface imperfections in the pin top surfaces 102 and/or opposing roller surfaces 121 and/or some compliance intentionally provided in the respective roller structures or roller carrying and/or driving mechanisms and structures, where an unfeasibly high amount of pressure in the nip would be required to express all material from the nipping regions between the tops of the aperturing pins and the opposing roller surface(s). This latter circumstance would be present in examples in which fiber components are present in the subject nonwoven web which are brittle or not substantially ductile, and which, as a result, are crushed and flattened beneath the pins but not expressed. Such examples may include nonwoven web materials constituted in part by fibers composed of non-thermoplastic materials, such as regenerated cellulose (e.g., rayon, viscose, lyocell, etc.). In some examples it may be desired to include with one or both of the rollers, or roller carrying and/or driving mechanisms and structures, features that provide limited compliance at a given pressure, i.e. allow the rollers to separate to a limited extent at the nip 110 at a given nip pressure, to delimit maximum pressure in the nip that is exerted on the pin surfaces 102, to reduce roller wear and chances of pin failure. As a result, a very thin/low caliper film 21*a* (shown in FIG. 10B, in one example) of unexpressed polymer and/or other fiber component material may remain within the apertures 321, as the apertured web 20 exits the nip 110. When component materials of the web constituent fibers are appropriately selected as described below, however, this thin film 21*a* will readily break away and out of the web, leaving behind an open aperture 321. The resulting apertures 321 may have about their perimeters 22 a fracture edge 24, which will be a remainder of the thin film 21*a* following break-away of the majority thereof. When the perimeter edges 103 of the pin top surfaces 102 are sharply defined, as described above, the amount of this film forming a fracture edge 24 will be minimized, i.e., the fracturing away of the film will desirably occur very close to the densified zone 23 and aperture perimeter 22.

In some circumstances the unexpressed film material may fracture away from the apertures 321 and adhere to either or both of the pin top surfaces 102 and the opposing roller surface(s) 106 as the nonwoven web 20 exits the nip 110. To address this, the system may be provided with online roller cleaning equipment 130*a* and/or 130*b*. Such roller cleaning equipment may consist of or include one or more scraper blades, brushes (which may themselves be configured to operate on counter-rotating rollers), a system of one or more pressurized air knives, water jets, or any combination thereof, or any other suitable roller cleaning equipment.

If component materials of nonwoven constituent fibers are suitably selected, the process and mechanism described above can be effective at imparting a nonwoven web with apertures at relatively high throughput rates, contributing to manufacturing efficiency.

As described herein, in some examples, a desired topsheet nonwoven web material may be constituted partially or entirely of bicomponent fibers, having first and second polymer components. In such examples, it may be desired that the respective polymer components have differing melt temperatures. When the melt temperatures of the respective components differ sufficiently, it is possible to operate the web aperturing system described above wherein one or both of the rollers 100, 120 is/are heated to a temperature(s) sufficient to cause one of the polymer components to melt, but not the other. Doing this causes the polymer component with the lower melt temperature to melt and readily flow out from beneath the aperturing pin top surfaces 102, beyond top surface perimeter edges 103. At the same time, the polymer component with the higher melt temperature will not melt, and is forced not only to plastically deform but also to fracture, as it is being expressed from beneath the pin top surfaces 102 in the nip 110. The thin film of unexpressed material that may be left behind as the web exits the nip 110 will be largely constituted by the component with the higher melting temperature—which will be, desirably, fractured into pieces which will easily fall or be drawn out of the apertures.

To achieve or enhance this effect, it may be desired that the first and second polymer components of the bicomponent fiber constituent have a difference in melt temperatures of at least about 44° C., more preferably at least about 72° C., and even more preferably at least about 100° C. This provides the operator with a broad range of temperatures to which it may heat one or both of the aperturing rollers, to cause melting of a first polymer component with a lower melt temperature, while avoiding melting of a second polymer component with a higher melt temperature.

In some examples such as those described herein, a suitable topsheet nonwoven may be constituted of sheath-core bicomponent fibers, in which polyethylene terephthalate (PET) constitutes the core component and polyethylene (PE) constitutes the sheath component. PET has a melt temperature of about 264° C., which is relatively high among potential thermoplastic polymer components deemed suitable for spinning fibers useful for purposes contemplated herein. This relatively high melt temperature leaves considerable breadth for selection of a second suitable polymer, since most currently known, suitable thermoplastic polymers suitable for spinning fibers useful for purposes herein have melt temperatures considerably lower than 264° C. Additionally, PET is relatively brittle, tending to fracture more than other suitable polymers, rather than plastically deform in a ductile manner, under heavy pressure, which is desirable for reasons described above. In contrast, PE has a melt temperate of about 110 to 130° C. (depending on specific form), and above the melt temperature will readily flow. This makes it suitable as a nonwoven constituent fiber component for purposes described above—including formation of a stable densified zone 23 surrounding apertures, that contribute to making the apertures and configuration/pattern thereof stable within the nonwoven in downstream processing and converting operations. PE also imparts other desirable characteristics to the nonwoven, as described above.

It is contemplated that the process described above may be applied simultaneously to two distinct nonwoven web materials together. The two distinct nonwoven web materials 10 may be conveyed together through a nip 110 between an aperturing roller 101 and an opposing roller 120, as described above. As the materials exit the nip, they will each have apertures 321 that are aligned along the z-direction. The respective nonwoven web materials will be bonded together to some extent, at the densified zones 23 surrounding the respective, aligned apertures 321, by thermoplastic fiber component material that has been melted and expressed from beneath the aperturing pins 101 in the nip, and then fused. For example, a topsheet nonwoven web material and a fluid management layer nonwoven material, as described herein or in references incorporated by reference herein, may be brought together and apertured in the manner described above. The fluid management layer may be constituted as described in, for example, U.S. Prov. App. Ser. No. 63/316,097. In some examples the fluid management layer may comprise any combination of monocomponent fibers, hollow monocomponent fibers, bicomponent fibers, cellulosic fibers, and regenerated cellulose fibers. The bicomponent fibers may spun to have a sheath-core configuration including a PET core component. The sheath component may be PE. The hollow monocomponent fibers may be spun of PET.

As noted, aperturing pins 101 can be formed with top surfaces 102 having a variety of surface areas and shapes, corresponding to the area and shape of the apertures one wishes to impart to the subject nonwoven web. It will be appreciated that a substantially circular-shaped aperture 321 in a web may be most efficient, per unit surface area, for providing a fluid passageway. Similarly, shapes that have aspect ratios (of machine direction dimension to cross-direction dimension) approaching 1:1 are relatively efficient, as compared to shapes having aspect ratios in which either dimension is substantially larger or smaller than the other. The process and equipment described herein may be configured to efficiently impart a pattern of apertures to a nonwoven web, wherein the apertures in the pattern have an average aspect ratio of from 2.5:1 to 1:2.5; more preferably 2:1 to 1:2; even more preferably from 1.5:1 to 1:1.5, still more preferably from 1.3:1 to 1:1.3, and most preferably from 1.2:1 to 1:1.2.

The process described above does not require that the web be substantially stretched in the machine or cross directions in a subsequent step, to open the apertures, following its exit from the nip.

Test and Measurement Methods

Caliper

The caliper, or thickness, of a test specimen is measured as the distance between a reference platform on which the specimen rests and a pressure foot that exerts a specified amount of pressure onto the specimen over a specified amount of time. All measurements are performed in a laboratory maintained at 23° C.±2 C.° and 50%±2% relative humidity and test specimens are conditioned in this environment for at least 2 hours prior to testing.

Caliper is measured with a manually-operated micrometer equipped with a pressure foot capable of exerting a steady pressure of 0.50 kPa±0.01 kPa onto the test specimen. The manually-operated micrometer is a dead-weight type instrument with readings accurate to 0.01 mm. A suitable instrument is Mitutoyo Series 543 ID-C Digimatic, available from VWR International, or equivalent. The pressure foot is a flat ground circular movable face with a diameter that is smaller than the test specimen and capable of exerting the required pressure. A suitable pressure foot has a diameter of 25.4 mm, however a smaller or larger foot can be used depending on the size of the specimen being measured. The test specimen is supported by a horizontal flat reference platform that is larger than and parallel to the surface of the pressure foot. The system is calibrated and operated per the manufacturer's instructions.

Obtain a test specimen by removing it from the pad, if necessary. When excising the test specimen from a pad, use care to not impart any contamination or distortion to the test specimen layer during the process. The test specimen is obtained from an area free of folds or wrinkles, and it must be larger than the pressure foot.

To measure caliper, first zero the micrometer against the horizontal flat reference platform. Place the test specimen on the platform with the test location centered below the pressure foot. Gently lower the pressure foot with a descent rate of 3.0 mm±1.0 mm per second until the full pressure is exerted onto the test specimen. Wait 5 seconds and then record the caliper of the test specimen to the nearest 0.001 mm. In like fashion, repeat for a total of ten replicate test specimens. Calculate the arithmetic mean for all caliper measurements and report as Caliper to the nearest 0.001 mm.

Basis Weight

The basis weight of a sample of sheet or web material is the mass (in grams) per unit area (in square meters) of a single layer of the material. If it is not otherwise known or available, basis weight may be measured using EDANA compendial method NWSP 130.1. The mass of the test sample is cut to a known area, and the mass of the sample is determined using an analytical balance accurate to 0.0001 grams. All measurements are performed in a laboratory maintained at 23° C.±2 C.° and 50%±2% relative humidity and test samples are conditioned in this environment for at least 2 hours prior to testing.

Measurements are made on test samples taken from rolls or sheets of the raw material, or test samples obtained from a material layer removed from a pad. When excising the material layer from the pad, use care to not impart any contamination or distortion to the layer during the process. The excised layer should be free from residual adhesive. To ensure that all adhesive is removed, soak the layer in a suitable solvent that will dissolve the adhesive without adversely affecting the material itself. One such solvent is THF (tetrahydrofuran, CAS 109-99-9, for general use, available from any convenient source). After the solvent soak, the material layer is allowed to thoroughly air dry in such a way that prevents undue stretching or other deformation of the material. After the material has dried, a test specimen is obtained. The test specimen must be as large as possible so that any inherent material variability is accounted for.

Measure the dimensions of the single layer test specimen using a calibrated steel metal ruler traceable to NIST, or equivalent. Calculate the Area of the test specimen and record to the nearest 0.0001 square meter. Use an analytical balance to obtain the Mass of the test specimen and record to the nearest 0.0001 gram. Calculate Basis Weight by dividing Mass (in grams) by Area (in square meters) and record to the nearest 0.01 grams per square meter (gsm). In like fashion, repeat for a total of ten replicate test specimens. Calculate the arithmetic mean for Basis Weight and report to the nearest 0.01 grams/square meter.

Material Compositional Analysis

If the information is not otherwise available, the quantitative chemical composition of a test specimen comprising a mixture of fiber types is determined using ISO 1833-1. All measurements are performed in a laboratory maintained at 23° C.±2 C.° and 50%±2% relative humidity.

Analysis is performed on test samples taken from rolls or sheets of the raw material, or test samples obtained from a material layer removed from a pad. When excising the material layer from the pad, use care to not impart any contamination or distortion to the layer during the process. The excised layer should be free from residual adhesive. To ensure that all adhesive is removed, soak the layer in a suitable solvent that will dissolve the adhesive without adversely affecting the material itself. One such solvent is THF (tetrahydrofuran, CAS 109-99-9, for general use, available from any convenient source). After the solvent soak, the material layer is allowed to thoroughly air dry in such a way that prevents undue stretching or other deformation of the material. After the material has dried, a test specimen is obtained and tested as per ISO 1833-1 to quantitatively determine its chemical composition.

Average Fiber Decitex (dtex) or Denier

Textile webs (e.g. woven, nonwoven, airlaid) are comprised of individual fibers of material. Fibers are characterized in one respect, by their linear mass density, reported in units of denier, or units of decitex. The decitex value is the mass in grams of a fiber present in 10,000 meters of that fiber. The denier value is the mass in grams of a fiber present in 9,000 meters of that fiber. The average decitex or denier value of the fibers within a web of material is often reported by manufacturers as part of a specification. If the average decitex or denier value of the fiber is not otherwise known or available, it can be calculated by measuring the cross-sectional area of the fiber via a suitable microscopy technique such as scanning electron microscopy (SEM), determining the composition of the fiber with suitable techniques such as FT-IR (Fourier Transform Infrared) spectroscopy and/or DSC (Dynamic Scanning calorimetry), and then using a literature value for density of the composition to calculate the mass in grams of the fiber present in 10,000 meters of the fiber (for decitex), or in 9,000 meters of the fiber (for denier).

All testing is performed in a room maintained at a temperature of 23° C.±2.0° C. and a relative humidity of 50%±2% and samples are conditioned under the same environmental conditions for at least 2 hours prior to testing.

If necessary, a representative sample of web material of interest can be excised from a pad. In this case, the web material is removed so as not to stretch, distort, or contaminate the sample.

SEM images are obtained and analyzed as follows to determine the cross-sectional area of a fiber. To analyze the cross section of a sample of web material, a test specimen is prepared as follows. Cut a specimen from the web that is approximately 1.5 cm (height) by 2.5 cm (length) and free from folds or wrinkles. Submerge the specimen in liquid nitrogen and fracture an edge along the specimen's length with a razor blade (VWR Single Edge Industrial Razor blade No. 9, surgical carbon steel). Sputter coat the specimen with gold and then adhere it to an SEM mount using double-sided conductive tape (Cu, 3M available from electron microscopy sciences). The specimen is oriented such that the cross section is as perpendicular as possible to the detector to minimize any oblique distortion in the measured cross sections. An SEM image is obtained at a resolution sufficient to clearly elucidate the cross sections of the fibers present in the specimen. Fiber cross sections may vary in shape, and some fibers may consist of a plurality of individual filaments. Regardless, the area of each of the fiber cross sections is determined (for example, using diameters for round fibers, major and minor axes for elliptical fibers, and image analysis for more complicated shapes). If fiber cross sections indicate inhomogeneous cross-sectional composition, the area of each recognizable component is recorded and dtex contributions are calculated for each component and subsequently summed. For example, if the fiber is bi-component, the cross-sectional area is measured separately for the core and sheath, and dtex contribution from core and sheath are each calculated and summed. If the fiber is hollow, the cross-sectional area excludes the inner portion of the fiber comprised of air, which does not appreciably contribute to fiber dtex. Altogether, at least 100 such measurements of cross-sectional area are made for each fiber type present in the specimen, and the arithmetic mean of the cross-sectional area $a_k$ for each are recorded in units of micrometers squared ($\mu m^2$) to the nearest 0.1 $\mu m^2$.

Fiber composition is determined using common characterization techniques such as FTIR spectroscopy. For more complicated fiber compositions (such as polypropylene core/polyethylene sheath bi-component fibers), a combination of common techniques (e.g. FTIR spectroscopy and DSC) may be required to fully characterize the fiber composition. Repeat this process for each fiber type present in the web material.

The average decitex $d_k$ value for each fiber type in the web material is calculated as follows:

$$d_k = 10000 m \times a_k \times \rho_k \times 10^{-6}$$

where $d_k$ is in units of grams (per calculated 10,000 meter length), $a_k$ is in units of $\mu m^2$, and $\rho_k$ is in units of grams per cubic centimeter (g/cm³). Average decitex is reported to the nearest 0.1 g (per calculated 10,000 meter length) along with the fiber type (e.g. polypropylene (PP), PET, cellulose, PP/PET bicomponent). The average denier value for each fiber type in the web material is its decitex $d_k$ value×0.9.

Apertures Percent Open Area Measurement Method

Percent open area is measured on images, of an apertured topsheet test specimen, acquired using a flatbed scanner. The scanner is capable of scanning in reflectance mode at a resolution of 2400 dpi and 8 bit grayscale. A suitable scanner is an Epson Perfection V750 Pro from Epson America Inc.

(Long Beach, California, USA) or one having substantially similar functionality. The scanner is interfaced with a computer running an image analysis program. A suitable program is ImageJ v. 1.47 (National Institute of Health, USA), or one having substantially similar functionality. The specimen images are distance calibrated against an acquired image of a ruler certified by NIST. To enable maximum contrast, the specimen is backed with an opaque, background sheet of uniformly black color, prior to acquiring the image. All measurement is performed in a conditioned room maintained at about 23±2° C. and about 50±2% relative humidity.

The Measurement Specimens are Prepared as Follows.

Obtain the required number of samples of the pad of interest. To obtain a measurement specimen, first identify the longitudinal and lateral axes of the pad and lightly mark them on the topsheet with a fine marker. Then tape the sample pad about its periphery (i.e., do not tape over regions underlaid by the fluid management layer), wearer-facing side up, in a flat configuration, to a horizontal flat work surface. Any elastic materials included (e.g., in leg cuffs), if present, may be cut to facilitate laying the pad out flat. The outer boundary of the region of the apertured topsheet overlying the absorbent structure of the pad is identified and marked. Now cut through the topsheet and any adhered underlying layers, about and through this marked outer boundary with a new razor blade or other comparable new, sharp, cutting implement. From this cut out portion, the test specimen of the apertured topsheet is then carefully separated and removed from the underlying layer(s) such that its longitudinal and lateral dimensions are not changed, to avoid distortion of the apertures. If the topsheet is adhered via adhesive to an underlying layer, before attempting separation apply any solvent suitable for dissolving the adhesive and allowing easy separation of the topsheet from underlying layer(s) without dissolving the polymer material (s) of fibers constituting the topsheet nonwoven web material. (In many examples, tetrahydrofuran (THF) can be a suitable solvent for this purpose. It is not a concern if the solvent dissolves applied surface finish coatings on the fibers, as long as it does not dissolve the polymer(s) constituting the fibers themselves.) Once the cut-out portion of the topsheet constituting the measurement specimen is removed, identify the wearer-facing side thereof. Five replicate measurement specimens obtained from five samples of the pads of interest, are prepared for measurement. The specimens are conditioned at about 23° C.±2 C.° and about 50%±2% relative humidity for 2 hours prior to imaging. If the topsheet is adhered by bonding to a subjacent fluid acquisition layer about the perimeters of apertures, keep the topsheet and fluid acquisition layer together as bonded.

Images are obtained as follows.

The ruler is placed on the scanner bed such that it is oriented parallel to the sides of the scanner glass. An image of the ruler (the calibration image) is acquired in reflectance mode at a resolution of 2400 dpi (approximately 94 pixels per mm) and in 8-bit grayscale. The calibration image is saved as an uncompressed TIFF format file. After obtaining the calibration image, the ruler is removed from the scanner glass and all specimens are scanned under the following scanning conditions.

A measurement specimen is placed onto the center of the scanner bed, lying flat, with the body-facing surface of the specimen facing the scanner's glass surface. The corners and edges of the specimen are secured such that its original longitudinal and lateral dimensions, as on the pad prior to removal, are retained. The specimen is oriented such that the long axis and short axis thereof are aligned parallel with and perpendicular to the sides of the scanner's glass surface, respectively. The black background is placed on top of the specimen, the scanner lid is closed, and a scanned image of the entire specimen is acquired with the same settings as used for the calibration image. The specimen image is saved as an uncompressed TIFF format file. The remaining four replicate specimens are scanned and saved in like manner.

The specimen image is analyzed as follows. Open the calibration image file in the image analysis program, and calibrate the image resolution using the imaged ruler to determine the number of pixels per millimeter. Now open the specimen image in the image analysis program, and set the distance scale using the image resolution determined from the calibration image. Now identify the central region 305 that is centered about the longitudinal and lateral axes of the pad, having sides 80 mm long parallel with the longitudinal axis 400 and ends 30 mm wide parallel with the lateral axis, and visually inspect the images of the apertures present within the central region. Now using the software tools, manually outline each of the apertures within the central region (and any partial portions thereof at the edges of the central region). The appropriate outlines will be drawn along visually discernible inside edges of the concentrations of displaced fibers 503 about the perimeters of the apertures. Stray individual fibers that may have escaped the main structure and/or the concentrations of displaced fibers about the perimeter, and cross into or through the main open area of the aperture (by way of illustrative example, stray individual fibers 16 shown in FIG. 12) are not considered subtractive from the aperture area for purposes herein.) Then use the software to measure the area within each discrete aperture outline (whole and partial) within the central region and record each to the nearest 0.01 mm², and calculate the sum total thereof. The area of each discrete aperture is defined as the x-y surface area within the visually discernable outline of the open region, created by mechanical penetration of the web and x-y direction displacement of fibers in an aperturing process, that creates the apertures through the web. (For example, refer to FIG. 12 where discrete aperture area 321 and visually discernable boundary 22 are depicted. The dark area of the depicted aperture is an image of black construction paper used as a backing to the specimen of which this particular image was made.) The sum of the areas of all of the apertures within the central region is recorded as Aperture Area to the nearest 0.01 mm². Now divide the Aperture Area by the central region area (1,600 mm²), then multiply by 100 and record as Percent Open Area to the nearest 0.1%.

In like manner, repeat the entire procedure for the remaining four replicate specimen images. Calculate the arithmetic mean of Percent Open Area across all five replicate specimens and report as Average Percent Open Area to the nearest 0.1%.

If desired, similar equipment and procedure may be employed to measure sizes and open areas of individual apertures and/or groups or paths of apertures inside or outside the central region. The person of ordinary skill in the art will readily understand how to adapt this method for such purpose.

It will be understood, however, that the method and equipment described above are not necessarily the only possible method and equipment that may be used to measure aperture size and aperture open area.

Non-Limiting Examples Contemplated Herein

In view of the foregoing description, the following non-limiting examples of combinations of features are contemplated herein. Where feasible, other features described herein may be included as well.

1. A feminine hygiene pad (300) having a longitudinal axis (400) oriented along a y-direction, a lateral axis (500) perpendicular to the longitudinal axis oriented along an x-direction, and a pad caliper measured along a z-direction orthogonal to the longitudinal and lateral axes, and comprising a liquid permeable topsheet (301) comprising a first fibrous nonwoven web, a backsheet (303) beneath the topsheet, and an absorbent structure (302) disposed between the topsheet and the backsheet, wherein:

the first fibrous nonwoven web comprises at least two arrangements (322, 323) of apertures (324a, 324b) therethrough, including a first arrangement (322) of first apertures (324a) having a first average size, and a second arrangement (323) of second apertures (324b) having a second average size, wherein the first average size is greater than the second average size;

wherein the first arrangement occupies a rectangular central region (305) that is 80 mm long by 20 mm wide, has forward and rearward sides and left and right sides, and is centered about the longitudinal axis (400) and lies on both forward and rearward sides of the lateral axis (500); the first average size is 0.4 mm$^2$ to 0.6 mm$^2$; and the central region has an Average Percent Open Area of 1 to 12 percent, more preferably 2 to 9 percent, and even more preferably 3 to 8 percent;

wherein the second arrangement occupies one or more regions laterally and/or longitudinally outboard of the central region, and the second average size is 0.05 mm$^2$ to 0.2 mm$^2$.

2. The feminine hygiene pad of example 1 wherein the second arrangement (323) comprises one or more paths of apertures of the second average size oriented generally along a longitudinal direction, lying laterally outboard of either side of the central region (305) and straddling the lateral axis (500).

3. The feminine hygiene pad of either of the preceding examples wherein the second arrangement (323) comprises paths of apertures of the second average size extending at least in part along a lateral direction, lying longitudinally outboard of either or both the forward and rearward ends of the central region (305) and straddling the longitudinal axis (400).

4. The feminine hygiene pad of any of the preceding examples, wherein the apertures in one or both of the first arrangement and second arrangement have an average aspect ratio of from 2.5:1 to 1:2.5; more preferably 2:1 to 1:2; even more preferably from 1.5:1 to 1:1.5, still more preferably from 1.3:1 to 1:1.3, and most preferably from 1.2:1 to 1:1.2.

5. The feminine hygiene pad of any of the preceding examples wherein the first nonwoven web comprises staple fibers, wherein some or all of the apertures in one or both the first and second arrangements are surrounded by densified agglomerations of material(s) (23) of which fibers of the first nonwoven web are composed, the materials having been plastically deformed and/or fused via z-application of localized z-direction direction compression and optionally, application of heat.

6. The feminine hygiene pad of example 5, wherein the first nonwoven web comprises a plurality of randomly distributed fiber-to-fiber bonds (17) therewithin, the fiber-to-fiber bonds not exhibiting effects of z-direction compression in the formation thereof.

7 The feminine hygiene pad of any of the preceding examples wherein the first nonwoven web comprises bicomponent fibers.

8. The feminine hygiene pad of example 7 wherein the bicomponent fibers are of a sheath-core bicomponent configuration having a sheath component and a core component.

9. The feminine hygiene pad of example 8 wherein the core component comprises a polymer selected from the group consisting of PET, PP and PE and combinations thereof, and preferably, PET.

10. The feminine hygiene pad of either of examples 8 or 9 wherein the sheath component comprises PE, preferably predominantly PE.

11. The feminine hygiene pad of any of the preceding examples, wherein constituent fibers of the first nonwoven web comprise fibers that are, in weight proportion, predominantly, substantially, or entirely hydrophobic, or rendered hydrophobic via fiber surface finish.

12. The feminine hygiene pad of any of the preceding examples wherein the first nonwoven web includes a first layer component having a first fiber constitution and a second layer component having a second fiber constitution differing from the first fiber constitution.

13. The feminine hygiene pad of example 12 wherein the first layer comprises predominantly hydrophobic fibers and the second layer comprises predominantly hydrophilic fibers.

14. The feminine hygiene pad of either of examples 12 or 13 wherein the second fiber constitution comprises a combination of bicomponent fibers and hollow monocomponent fibers.

15. The feminine hygiene pad of example 14 wherein the hollow monocomponent fibers comprise PET.

16. The feminine hygiene pad of any of examples 12-15 wherein the second fiber constitution comprises cellulosic fibers.

17. The feminine hygiene pad of example 16 wherein the cellulosic fibers comprise regenerated cellulose.

18. The feminine hygiene pad of any of the preceding examples comprising a fluid management layer (302a) disposed beneath the topsheet (301), the fluid management layer comprising a second fibrous nonwoven web, wherein the apertures through the first nonwoven web extend in a z-direction at least partially through the second fibrous nonwoven web, wherein the first fibrous nonwoven web and the second fibrous nonwoven web are at least partially bonded together about perimeters 22 of apertures extending through each, wherein material at the perimeters of apertures through the topsheet is recessed along a z-direction from the uppermost surface regions of the topsheet.

19. A process for producing topsheets for feminine hygiene pads, the pads and topsheets having prescribed lengths, widths, longitudinal axes (400) and lateral axes (500), comprising the steps of:

providing a nonwoven web (10) and conveying it along a machine direction (MD);

providing a pair of aperturing rollers (100, 120) having a nip (110) therebetween, the nip being oriented along a cross direction (CD);

passing the nonwoven web along the machine direction through the nip, and thereby sequentially and repeatedly imparting a pitched pattern of apertures through the nonwoven web as it moves along the machine direction, the pattern comprising:

at least two arrangements (322, 323) of apertures (324$a$, 324$b$) therethrough, including a first arrangement (322) of first apertures (324$a$) having a first average size, and a second arrangement (323) of second apertures (324$b$) having a second average size, wherein the first average size is greater than the second average size, wherein:

the first arrangement occupies a rectangular central region (305) that is 80 mm long by 20 mm wide, has forward and rearward sides and left and right sides, and is centered about the longitudinal axis (400) and lies on both forward and rearward sides of the lateral axis (500); the first average size is 0.4 mm$^2$ to 0.6 mm$^2$; and the central region has an Average Percent Open Area of 1 to 12 percent, more preferably 2 to 9 percent, and even more preferably 3 to 8 percent;

the second arrangement occupies one or more regions laterally and/or longitudinally outboard of the central region, and the second average size is 0.05 mm$^2$ to 0.2 mm$^2$.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A feminine hygiene pad having a longitudinal axis oriented along a y-direction, a lateral axis perpendicular to the longitudinal axis oriented along an x-direction, and a pad caliper measured along a z-direction orthogonal to the longitudinal and lateral axes, and comprising a liquid permeable topsheet comprising a first fibrous nonwoven web, a backsheet beneath the topsheet, and an absorbent structure disposed between the topsheet and the backsheet, wherein:

the first fibrous nonwoven web comprises at least two arrangements of apertures therethrough, including a first arrangement of first apertures having a first average size, and a second arrangement of second apertures having a second average size, wherein the first average size is greater than the second average size;

wherein the first arrangement occupies a rectangular central region that is 80 mm long by 20 mm wide, has forward and rearward sides and left and right sides, and is centered about the longitudinal axis and lies on both forward and rearward sides of the lateral axis; the first average size is 0.4 mm$^2$ to 0.6 mm$^2$; and the central region has an Average Percent Open Area of 1 to 12 percent;

wherein the second arrangement occupies one or more regions longitudinally outboard of the central region, and the second average size is 0.05 mm$^2$ to 0.2 mm$^2$; and wherein the second arrangement comprises one or more paths of the second apertures, wherein each of the one or more paths comprises a group of the second apertures such that for each of the one or more paths:

each second aperture of the group is located a distance of not greater than three times a largest dimension of the second apertures in the group from its immediate neighbor second aperture in the group; or there is no break angle among the second apertures of the group that is less than 120 degrees, wherein the break angle is at an intersection of path lines through geometric centers of immediate neighboring second apertures in the group.

2. The feminine hygiene pad of claim 1 wherein the second arrangement further occupies one or more regions laterally outboard of the central region, wherein the second arrangement comprises the one or more paths of apertures of the second average size oriented generally along a longitudinal direction, lying laterally outboard of either side of the central region and straddling the lateral axis.

3. The feminine hygiene pad of claim 1 wherein the second arrangement comprises the one or more paths of apertures of the second average size extending at least in part along a lateral direction, lying longitudinally outboard of either or both the forward and rearward ends of the central region and straddling the longitudinal axis.

4. The feminine hygiene pad of claim 3, wherein the paths of the apertures of the second arrangement extend over the longitudinal axis of the feminine hygiene pad along the lateral direction and wherein the paths of the apertures of the second arrangement extend along a periphery of the absorbent structure and enclose the rectangular central region.

5. The feminine hygiene pad of claim 1 wherein the apertures in one or both of the first arrangement and second arrangement have an average aspect ratio of from 2.5:1 to 1:2.5.

6. The feminine hygiene pad of claim 1 wherein the first nonwoven web comprises staple fibers, wherein some or all of the apertures in one or both the first and second arrangements are surrounded by densified agglomerations of material(s) of which fibers of the first nonwoven web are composed, the materials having been plastically deformed and/or fused via z-application of localized z-direction direction compression.

7. The feminine hygiene pad of claim 6, wherein the first nonwoven web comprises a plurality of randomly distributed fiber-to-fiber bonds therewithin, the fiber-to-fiber bonds not exhibiting effects of z-direction compression in the formation thereof.

8. The feminine hygiene pad of claim 1, wherein the first nonwoven web comprises bicomponent fibers.

9. The feminine hygiene pad of claim 8 wherein the bicomponent fibers are of a sheath-core bicomponent configuration having a sheath component and a core component.

10. The feminine hygiene pad of claim 9 wherein the core component comprises a polymer selected from the group consisting of PET, PP and PE and combinations thereof.

11. The feminine hygiene pad of claim 9 wherein the sheath component comprises PE.

12. The feminine hygiene pad of claim 1 wherein constituent fibers of the first nonwoven web comprise fibers that are, in weight proportion, substantially hydrophobic, or rendered hydrophobic via fiber surface finish.

13. The feminine hygiene pad of claim 1 wherein the first nonwoven web includes a first layer component having a first fiber constitution and a second layer component having a second fiber constitution differing from the first fiber constitution.

14. The feminine hygiene pad of claim 13 wherein the first layer comprises predominantly hydrophobic fibers and the second layer comprises predominantly hydrophilic fibers.

15. The feminine hygiene pad of claim 13 wherein the second fiber constitution comprises a combination of bicomponent fibers and hollow monocomponent fibers.

16. The feminine hygiene pad of claim 15 wherein the hollow monocomponent fibers comprise PET.

17. The feminine hygiene pad of claim 13 wherein the second fiber constitution comprises cellulosic fibers.

18. The feminine hygiene pad of claim 17 wherein the cellulosic fibers comprise regenerated cellulose.

19. The feminine hygiene pad of claim 1 comprising a fluid management layer disposed beneath the topsheet, the fluid management layer comprising a second fibrous nonwoven web, wherein the apertures through the first nonwoven web extend in a z-direction at least partially through the second fibrous nonwoven web, wherein the first fibrous nonwoven web and the second fibrous nonwoven web are at least partially bonded together about perimeters of apertures extending through each, wherein material at the perimeters of apertures through the topsheet is recessed along a z-direction from the uppermost surface regions of the topsheet.

20. The feminine hygiene pad of claim 1, wherein the one or more paths of apertures of the second average size provide:

an actual effect comprising a barrier structure to prevent fluid from migrating across the topsheet to locations outside the one or more paths; and a visual effect that imparts the pad with a pillowy visual appearance.

21. The feminine hygiene pad of claim 1, wherein the 1 percent of the Average Percent Open Area is a lower limit of the Average Percent Open Area and is selected to achieve efficacy and performance in the first apertures for fluid acquisition and wherein the 12 percent of the Average Percent Open Area is an upper limit of the Average Percent Open Area that is selected to achieve efficacy and performance in the first apertures for fluid retention and reducing a visibility of staining in the absorbent structure.

22. A process for producing topsheets for feminine hygiene pads, the pads and topsheets having prescribed lengths, widths, longitudinal axes and lateral axes, comprising the steps of:

providing a nonwoven web and conveying it along a machine direction (MD);

providing a pair of aperturing rollers having a nip therebetween, the nip being oriented along a cross direction (CD);

passing the nonwoven web along the machine direction through the nip, and thereby sequentially and repeatedly imparting a pitched pattern of apertures through the nonwoven web as it moves along the machine direction, the pattern comprising:

at least two arrangements of apertures therethrough, including a first arrangement of first apertures having a first average size, and a second arrangement of second apertures having a second average size, wherein the first average size is greater than the second average size, wherein:

the first arrangement occupies a rectangular central region that is 80 mm long by 20 mm wide, has forward and rearward sides and left and right sides, and is centered about the longitudinal axis and lies on both forward and rearward sides of the lateral axis; the first average size is 0.4 mm$^2$ to 0.6 mm$^2$; and the central region has an Average Percent Open Area of 1 to 12 percent;

the second arrangement occupies one or more regions longitudinally outboard of the central region, and the second average size is 0.05 mm$^2$ to 0.2 mm$^2$; and wherein the second arrangement comprises one or more paths of the second apertures, wherein each of the one or more paths comprises a group of the second apertures such that for each of the one or more paths:

each second aperture of the group is located a distance of not greater than three times a largest dimension of the second apertures in the group from its immediate neighbor second aperture in the group; or there is no break angle among the second apertures of the group that is less than 120 degrees, wherein the break angle is at an intersection of path lines through geometric centers of immediate neighboring second apertures in the group.

23. A feminine hygiene pad having a longitudinal axis oriented along a y-direction, a lateral axis perpendicular to the longitudinal axis oriented along an x-direction, and a pad caliper measured along a z-direction orthogonal to the longitudinal and lateral axes, and comprising a liquid permeable topsheet comprising a first fibrous nonwoven web, a backsheet beneath the topsheet, and an absorbent structure disposed between the topsheet and the backsheet, wherein:

the first fibrous nonwoven web comprises at least two arrangements of apertures therethrough, including a first arrangement of first apertures having a first average size, and a second arrangement of second apertures having a second average size, wherein the first average size is greater than the second average size;

wherein the first arrangement occupies a rectangular central region that is 80 mm long by 20 mm wide, has forward and rearward sides and left and right sides, wherein the forward side of the rectangular central region is longitudinally inboard of a forward side of the absorbent structure and wherein the rearward side of the rectangular central region is longitudinally inboard of a rearward side of the absorbent structure and wherein the rectangular central region is centered about the longitudinal axis and lies on both forward and rearward sides of the lateral axis; the first average size is 0.4 mm$^2$ to 0.6 mm$^2$; and the central region has an Average Percent Open Area between a lower limit and an upper limit, wherein a value of the lower limit is selected to achieve efficacy and performance in the first arrangement of the first apertures for fluid acquisition and wherein a value of the upper limit is selected to achieve efficacy and performance in the first arrangement of the first apertures for fluid retention and reducing a visibility of staining in the absorbent structure;

wherein the second arrangement occupies one or more regions longitudinally outboard of the central region and comprising paths of apertures of the second average size extending in part along a lateral direction over the longitudinal axis of the feminine hygiene pad, wherein each aperture in each of the paths is located a distance from its immediate neighbor aperture that is not greater than three times a largest dimension of the apertures of the second average size, wherein there is no break angle among the apertures of each of the paths that is less than 120 degrees, wherein the break angle is at an intersection of path lines through geometric centers of immediate neighboring apertures in each of the paths and wherein the second average size is 0.05 mm$^2$ to 0.2 mm$^2$.

* * * * *